US005800982A

United States Patent [19]
Hasegawa et al.

[11] Patent Number: 5,800,982
[45] Date of Patent: Sep. 1, 1998

[54] ANTIGENIC PEPTIDES FOR GROWING HEPATITIS C VIRUS, KIT COMPRISING THE SAME AND METHODS FOR ITS GROUPING USING THE SAME

[75] Inventors: Akira Hasegawa, Sakado; Noboru Maki; Shintaro Yagi, both of Iruma-gun; Tomiko Kashiwakuma, Tokyo; Kenjiro Yamaguchi, Iruma; Naoko Ikeguchi, Higashi-Kurume; Tomoko Kobayashi, Kami-Fukuoka; Chiaki Senoo, Iruma-gun, all of Japan

[73] Assignee: Tonen Corporation, Tokyo, Japan

[21] Appl. No.: 685,764

[22] Filed: Jul. 24, 1996

Related U.S. Application Data

[63] Continuation of Ser. No. 92,192, Jul. 15, 1993, abandoned.

[30] Foreign Application Priority Data

| Jul. 16, 1992 | [JP] | Japan | 4-212061 |
| Oct. 30, 1992 | [JP] | Japan | 4-316634 |
| Oct. 30, 1992 | [JP] | Japan | 4-316635 |
| Apr. 30, 1993 | [JP] | Japan | 5-104754 |

[51] Int. Cl.$^6$ .............. C12Q 1/70; C07K 14/18; A61K 39/29
[52] U.S. Cl. .............. 435/5; 530/324; 530/325; 530/326; 424/228.1
[58] Field of Search .............. 435/5; 530/324, 530/325, 326; 424/228.1

[56] References Cited

U.S. PATENT DOCUMENTS 5,247,067 9/1993 Arima et al. .............. 530/324

FOREIGN PATENT DOCUMENTS

| 468 657 A2 | 1/1992 | European Pat. Off. | |
| 484 787 A2 | 5/1992 | European Pat. Off. | |
| 0489968 | 6/1992 | European Pat. Off. | C07K 7/10 |
| WO 93/01210 | 1/1993 | WIPO | |
| WO 93/10239 | 5/1993 | WIPO | |
| WO 93/11158 | 6/1993 | WIPO | |

OTHER PUBLICATIONS

Stuyver et al., "Analysis of the Putative E1 Envelope and NSAa . . . ," Biochem Biophys Res Comm 192: 635–641 (1993).

Geyson et al., "Cognitive Features of Continuous Antigenic . . . , " J Molec Recog 1: 32–41 (1988).

Houghten et al., "The Use of Synthetic Peptide Combinatorial . . . , " BioTechniques 13: 412–421 (1992).

Sallberg et al., "Immune Response to a Single Peptide . . . , " Immunol Lett 33: 27–34 (1992).

K. Tsukiyama–Kohara et al., Virology, "Antigenicities of Group I and II Hepatitis C Virus Polypeptides—Molecular Basis of Diagnosis", 192, pp. 430–437 (1993).

P. Simmonds et al., Journal of Clinical Microbiology, "Mapping of Serotype–Specific, Immunodominant Epitopes in the NS–4 Region of Hepatitis C Virus (HCV): Use of Type–Specific Peptides to Serologically Differentiate Infections with HCV Types 1, 2 and 3", 31:6, pp. 1493–1503, (Jun. 1993).

Kyoko Tsukiyama–Kohara et al., Virus Genes, "A Second Group of Hepatitis C Viruses", 5:3, pp. 243–254, (1991).

Hiroaki Okamoto et al., Virology, "Full–Length Sequence of a Hepatitis C Virus Genome Having Poor Homology to Reported Isolates: Comparative Study of Four Distinct Geneotypes", 188, pp. 331–341 (1992).

Primary Examiner—Michael P. Woodward
Attorney, Agent, or Firm—David G. Conlin; Linda M. Buckley

[57] ABSTRACT

The present invention relates to an NS4-related antigenic peptide capable of reacting specifically with antibodies directed against Group I of hepatitis C virus (HCV); to an NS4-related antigenic peptide capable of reacting specifically with antibodies directed against Group II of HCV; to a kit for identifying HCV Groups I or II which comprises said peptides in separate sections; and to methods for grouping HCV. The peptides of the present invention can be used to detect HCV Groups I or II specifically as well as the detection of patients having the mixed infection, by which HCV Group II-infected patients can receive early interferon treatment effectively. The peptides are also useful for diagnosis of HCV infection.

8 Claims, 3 Drawing Sheets

```
C14-1    : EFTTGSVVIVGRIILSGKPAVIPDREALYQEFDEMEECASHLPYIEQGMQLAEQFKQRALGLL
           ****************  **********************************************
C14-1-2  : EFTTGSVVIVGRIILSGRPAVIPDREVLYREFDEMEECASHLPYIEQGMQLAEQFKQKALGLLQTATKHAEAAAPVVESKWRALETF

C14-2    : EFATGCISIIGRLHLNDRVVVTPDKEILYEAFDEMEECASKAALIEEGQRMAEMLKSKIQGLL
           ****  **  ********* **  **** ****************  *********************
C14-2-2  : EFATGCVSIIGRLHINQRAVVAPDKEVLYEAFDEMEECASRAALIEEGQRIAEMLKSKIQGLLQQASKQAQDIKPAVQTSWPKVEQF
```

FIG. 1

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 63 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Glu Phe Thr Thr Gly Ser Val Val Ile Val Gly Arg Ile Ile Leu Ser
1               5                   10                  15

Gly Lys Pro Ala Val Ile Pro Asp Arg Glu Ala Leu Tyr Gln Glu Phe
            20                  25                  30

Asp Glu Met Glu Glu Cys Ala Ser His Leu Pro Tyr Ile Glu Gln Gly
        35                  40                  45

Met Gln Leu Ala Glu Gln Phe Lys Gln Arg Ala Leu Gly Leu Leu
    50                  55                  60
```

( 2 ) INFORMATION FOR SEQ ID NO:2:

( i ) SEQUENCE CHARACTERISTICS:
        ( A ) LENGTH: 87 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Glu Phe Thr Thr Gly Ser Val Val Ile Val Gly Arg Ile Ile Leu Ser
1               5                   10                  15

Gly Arg Pro Ala Val Ile Pro Asp Arg Glu Val Leu Tyr Arg Glu Phe
            20                  25                  30

Asp Glu Met Glu Glu Cys Ala Ser His Leu Pro Tyr Ile Glu Gln Gly
        35                  40                  45

Met Gln Leu Ala Glu Gln Phe Lys Gln Lys Ala Leu Gly Leu Leu Gln
    50                  55                  60

Thr Ala Thr Lys His Ala Glu Ala Ala Ala Pro Val Val Glu Ser Lys
65                  70                  75                  80

Trp Arg Ala Leu Glu Thr Phe
                85
```

( 2 ) INFORMATION FOR SEQ ID NO:3:

( i ) SEQUENCE CHARACTERISTICS:
        ( A ) LENGTH: 63 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Glu Phe Ala Thr Gly Cys Ile Ser Ile Ile Gly Arg Leu His Leu Asn
 1               5                  10                  15
Asp Arg Val Val Val Thr Pro Asp Lys Glu Ile Leu Tyr Glu Ala Phe
            20                  25                  30
Asp Glu Met Glu Glu Cys Ala Ser Lys Ala Ala Leu Ile Glu Glu Gly
            35                  40                  45
Gln Arg Met Ala Glu Met Leu Lys Ser Lys Ile Gln Gly Leu Leu
        50                  55                  60
```

( 2 ) INFORMATION FOR SEQ ID NO:4:

( i ) SEQUENCE CHARACTERISTICS:
        ( A ) LENGTH: 87 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Glu Phe Ala Thr Gly Cys Val Ser Ile Ile Gly Arg Leu His Ile Asn
 1               5                  10                  15
Gln Arg Ala Val Val Ala Pro Asp Lys Glu Val Leu Tyr Glu Ala Phe
            20                  25                  30
Asp Glu Met Glu Glu Cys Ala Ser Arg Ala Ala Leu Ile Glu Glu Gly
            35                  40                  45
Gln Arg Ile Ala Glu Met Leu Lys Ser Lys Ile Gln Gly Leu Leu Gln
        50                  55                  60
Gln Ala Ser Lys Gln Ala Gln Asp Ile Lys Pro Ala Val Gln Thr Ser
65                  70                  75                  80
Trp Pro Lys Val Glu Gln Phe
                85
```

( 2 ) INFORMATION FOR SEQ ID NO:5:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: linear ( i i ) MOLECULE TYPE: cDNA to genomic RNA ( v i ) ORIGINAL SOURCE:
        ( A ) ORGANISM: HEPATITIS C VIRUS ( x i ) SEQUENCE DESCRIPTION: SEQ ID NO:5:

```
GAATTCACGA CAGGCAGCGT GGTCATTGTG GGCAGAATCA TCTTGTCCGG GAAGCCGGCT    60
GTTATCCCCG ACAGGGAAGC TCTATACCAG GAGTTCGATG AGATGGAAGA GTGCGCCTCG   120
CACCTCCCAT ACATCGAGCA GGGAATGCAG CTCGCCGAGC AATTCAAGCA GAGGGCGCTC   180
GGATTGCTG                                                           189
```

( 2 ) INFORMATION FOR SEQ ID NO:6:

( i ) SEQUENCE CHARACTERISTICS:
( A ) LENGTH: 267 base pairs
( B ) TYPE: nucleic acid
( C ) STRANDEDNESS: double
( D ) TOPOLOGY: linear ( i i ) MOLECULE TYPE: cDNA to genomic RNA ( v i ) ORIGINAL SOURCE:
( A ) ORGANISM: HEPATITIS C VIRUS ( x i ) SEQUENCE DESCRIPTION: SEQ ID NO:6:

| | | | | | | |
|---|---|---|---|---|---|---|
| GAATTCACAA | CAGGCAGTGT | GGTCATTGTG | GGTAGGATCA | TCTTGTCCGG | GAGGCCGGCT | 60 |
| GTTATTCCCG | ACAGGGAAGT | CCTCTACCGG | GAGTTCGATG | AGATGGAAGA | GTGCGCCTCA | 120 |
| CACCTCCCTT | ACATCGAACA | GGGAATGCAG | CTTGCCGAGC | AATTCAAGCA | GAAGGCGCTC | 180 |
| GGATTGCTGC | AAACAGCCAC | CAAGCACGCG | GAGGCTGCTG | CTCCCGTGGT | AGAATCCAAG | 240 |
| TGGCGAGCCC | TTGAGACCTT | CTAATGA | | | | 267 |

( 2 ) INFORMATION FOR SEQ ID NO:7:

( i ) SEQUENCE CHARACTERISTICS:
( A ) LENGTH: 189 base pairs
( B ) TYPE: nucleic acid
( C ) STRANDEDNESS: double
( D ) TOPOLOGY: linear ( i i ) MOLECULE TYPE: cDNA to genomic RNA ( v i ) ORIGINAL SOURCE:
( A ) ORGANISM: HEPATITIS C VIRUS ( x i ) SEQUENCE DESCRIPTION: SEQ ID NO:7:

| | | | | | | |
|---|---|---|---|---|---|---|
| GAATTCGCGA | CCGGCTGCAT | TTCCATCATT | GGCCGCCTTC | ACCTGAATGA | TCGGGTGGTC | 60 |
| GTGACCCCTG | ATAAGGAAAT | TTATATGAG | GCCTTTGATG | AGATGGAAGA | GTGCGCCTCC | 120 |
| AAAGCCGCCC | TCATTGAGGA | AGGGCAGCGG | ATGGCGGAGA | TGCTGAAGTC | TAAAATACAA | 180 |
| GGCCTCTTA | | | | | | 189 |

( 2 ) INFORMATION FOR SEQ ID NO:8:

( i ) SEQUENCE CHARACTERISTICS:
( A ) LENGTH: 261 base pairs
( B ) TYPE: nucleic acid
( C ) STRANDEDNESS: double
( D ) TOPOLOGY: linear ( i i ) MOLECULE TYPE: cDNA to genomic RNA ( v i ) ORIGINAL SOURCE:
( A ) ORGANISM: HEPATITIS C VIRUS ( x i ) SEQUENCE DESCRIPTION: SEQ ID NO:8:

| | | | | | | |
|---|---|---|---|---|---|---|
| GAATTCGCGA | CCGGGTGTGT | TTCCATCATC | GGCCGTTTGC | ATATCAACCA | GCGAGCCGTC | 60 |
| GTTGCACCGG | ACAAGGAGGT | CCTTTATGAG | GCTTTTGATG | AGATGGAGGA | ATGTGCCTCT | 120 |
| AGAGCGGCTC | TCATTGAAGA | GGGGCAACGG | ATAGCCGAGA | TGCTGAAGTC | CAAGATCCAG | 180 |
| GGCTTACTGC | AGCAAGCCTC | CAAGCAGGCC | CAAGACATAA | AACCCGCTGT | GCAGACTTCA | 240 |
| TGGCCCAAGG | TGGAGCAGTT | C | | | | 261 |

( 2 ) INFORMATION FOR SEQ ID NO:9:

( i ) SEQUENCE CHARACTERISTICS:
( A ) LENGTH: 667 base pairs
( B ) TYPE: nucleic acid (C) STRANDEDNESS: double
(D) TOPOLOGY: linear (ii) MOLECULE TYPE: cDNA to genomic RNA (ix) FEATURE:
    (A) NAME/KEY: CDS
    (B) LOCATION: 2..667

(vi) ORIGINAL SOURCE:
    (A) ORGANISM: HEPATITIS C VIRUS (xi) SEQUENCE DESCRIPTION: SEQ ID NO:9:

```
A  ACA  AAG  CAG  TCG  GGG  GAG  AAC  TTC  GCT  TAT  TTG  GCA  GCC  TAT  CAG              46
   Thr  Lys  Gln  Ser  Gly  Glu  Asn  Phe  Ala  Tyr  Leu  Ala  Ala  Tyr  Gln
   1              5                        10                       15

GCT  ACA  GTG  TGC  GCC  AGG  GCG  AGA  GCC  CCC  CCC  CCG  TCT  TGG  GAC  GTC             94
Ala  Thr  Val  Cys  Ala  Arg  Ala  Arg  Ala  Pro  Pro  Pro  Ser  Trp  Asp  Val
                    20                       25                       30

ATG  TGG  AAG  TGC  TTG  ACT  CGA  CTT  AAG  CCC  ACG  CTC  GTG  GGC  CCT  ACA             142
Met  Trp  Lys  Cys  Leu  Thr  Arg  Leu  Lys  Pro  Thr  Leu  Val  Gly  Pro  Thr
               35                       40                       45

CCT  CTC  CTG  TAT  CGT  TTG  GGC  TCT  GTT  ACC  AAC  GAG  GTC  ACC  CTC  ACA             190
Pro  Leu  Leu  Tyr  Arg  Leu  Gly  Ser  Val  Thr  Asn  Glu  Val  Thr  Leu  Thr
          50                       55                       60

CAT  CCT  GTG  ACA  AAA  TAC  ATC  GCC  ACG  TGC  ATG  CAA  GCT  GAC  CTC  GAG             238
His  Pro  Val  Thr  Lys  Tyr  Ile  Ala  Thr  Cys  Met  Gln  Ala  Asp  Leu  Glu
     65                       70                       75

GTC  ATG  ACC  AGC  ACA  TGG  GTC  CTG  GCC  GGG  GGA  GTC  TTG  GCA  GCC  GTC             286
Val  Met  Thr  Ser  Thr  Trp  Val  Leu  Ala  Gly  Gly  Val  Leu  Ala  Ala  Val
80                       85                       90                       95

GCT  CGT  TAT  TGC  CTG  GCG  ACC  GGG  TGT  GTT  TCC  ATC  ATC  GGC  CGT  TTG             334
Ala  Arg  Tyr  Cys  Leu  Ala  Thr  Gly  Cys  Val  Ser  Ile  Ile  Gly  Arg  Leu
                    100                      105                      110

CAT  ATC  AAC  CAG  CGA  GCC  GTC  GTT  GCA  CCG  GAC  AAG  GAG  GTC  CTT  TAT             382
His  Ile  Asn  Gln  Arg  Ala  Val  Val  Ala  Pro  Asp  Lys  Glu  Val  Leu  Tyr
               115                      120                      125

GAG  GCT  TTT  GAT  GAG  ATG  GAG  GAA  TGT  GCC  TCT  AGA  GCG  GCT  CTC  ATT             430
Glu  Ala  Phe  Asp  Glu  Met  Glu  Glu  Cys  Ala  Ser  Arg  Ala  Ala  Leu  Ile
          130                      135                      140

GAA  CAG  GGG  CAA  CGG  ATA  GCC  GAG  ATG  CTG  AAG  TCC  AAG  ATC  CAG  GGC             478
Glu  Gln  Gly  Gln  Arg  Ile  Ala  Glu  Met  Leu  Lys  Ser  Lys  Ile  Gln  Gly
     145                      150                      155

TTA  CTG  CAG  CAA  GCC  TCC  AAG  CAG  GCC  CAA  GAC  ATA  AAA  CCC  GCT  GTG             526
Leu  Leu  Gln  Gln  Ala  Ser  Lys  Gln  Ala  Gln  Asp  Ile  Lys  Pro  Ala  Val
160                      165                      170                      175

CAG  ACT  TCA  TGG  CCC  AAG  GTG  GAG  CAG  TTC  TGG  GCC  AAG  CAC  ATG  TGG             574
Gln  Thr  Ser  Trp  Pro  Lys  Val  Glu  Gln  Phe  Trp  Ala  Lys  His  Met  Trp
                    180                      185                      190

AAC  TTC  ATC  AGT  GGC  ATC  CAA  TAC  CTT  GCA  GGA  CTG  TCA  ACA  CTG  CCG             622
Asn  Phe  Ile  Ser  Gly  Ile  Gln  Tyr  Leu  Ala  Gly  Leu  Ser  Thr  Leu  Pro
               195                      200                      205

GGG  AAC  CCC  GCT  GTG  GCT  TCC  ATG  ATG  GCA  TTC  AGT  GCC  GCT  CTC                  667
Gly  Asn  Pro  Ala  Val  Ala  Ser  Met  Met  Ala  Phe  Ser  Ala  Ala  Leu
          210                      215                      220
```

(2) INFORMATION FOR SEQ ID NO:10:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE:

( x i ) SEQUENCE DESCRIPTION: SEQ ID NO:10:

AGGTCGTCAC TAGCACCTGG GTGC 24

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:11:

TGTATCCCGC TGATGAAGTT CCAC 24

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:12:

GAATTCACGA CAGGCAGCGT GGTC 24

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:13:

CTATTACAGC AATCCGAGCG CCCT 24

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:14:

GGCTATACCG GTGACTTTGA 20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:15:

GTCTCAGCTC CCTTCCGATC 20

( 2 ) INFORMATION FOR SEQ ID NO:16:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:16:

GATCTACTGC TAACACATGT GTCA     24

( 2 ) INFORMATION FOR SEQ ID NO:17:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:17:

GCGAATTCAC AACAGGCAGT GTGGTCATT     29

( 2 ) INFORMATION FOR SEQ ID NO:18:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:18:

GCTCATTAGA AGGTCTCAAG GGCTCGCCA     29

( 2 ) INFORMATION FOR SEQ ID NO:19:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:19:

GAATTCGCGA CCGGCTGCAT TTCC     24

( 2 ) INFORMATION FOR SEQ ID NO:20:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:20:

CTATTATAAG AGGCCTTGTA TTTT     24

( 2 ) INFORMATION FOR SEQ ID NO:21:

( i ) SEQUENCE CHARACTERISTICS:
    ( A ) LENGTH: 24 base pairs ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:21:

GAATTCCCTG ATAAGGAAAT TTTA                    24

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:22:

CTATTATAAG AGGCCTTGTA TTTT                    24

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:23:

GGATCACCGG TGACTTTGA                          19

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:24:

CCCCAAAATG TTGAGAAGGA TA                      22

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:25:

GATGCCCACT TCCTCTCCCA                         20

( 2 ) INFORMATION FOR SEQ ID NO:26:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:26:

GTGCTAGTTG ACAACGGACT GGT 23

( 2 ) INFORMATION FOR SEQ ID NO:27:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:27:

GCGAATTCGC GACCGGGTGT GTTTCCAT 28

( 2 ) INFORMATION FOR SEQ ID NO:28:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:28:

TCATTAGAAC TGCTCCACCT TGGGCCA 27

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:29:

GGATACACCG GTGACTTTGA 20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:30:

TGCATGCACG TGGCGATGTA 20

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:31:

GATGCCCACT TCCTCTCCCA 20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:32:

GTCAGGGTAA CCTCGTTGGT        20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:33:

GGCTATACCG GCGACTTCGA        20

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:34:

GACATGCATG TCATGATGTA        20

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:35:

GATCGACTGT AACACATGTG        20

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:36:

CACATTTGAT CCCACGATGG        20

ANTIGENIC PEPTIDES FOR GROWING HEPATITIS C VIRUS, KIT COMPRISING THE SAME AND METHODS FOR ITS GROUPING USING THE SAME

This is a continuation of application Ser. No. 08/092,192, filed Jul. 15, 1993, now abandoned.

The present invention relates to antigenic peptides for grouping hepatitis C virus, to a kit comprising the peptides, and to methods for its grouping using the peptides.

BACKGROUND OF THE INVENTION

Non-A, non-B hepatitis, generally referred to as hepatitis C, is an infectious hepatitis caused by a certain virus other than hepatitis A and B viruses, and often led to chronic hepatitis and subsequently to hepatic cirrhosis or cancer at a high rate, and therefore this disease has become a serious social problem. Its identifiable diagnosis is very hard because an expressed amount of the virus is extremely small in patient or healthy carrier bodies, and because it is not known whether the hepatitis-causing virus is present as one type or two or more types. Until recently, the diagnosis of non-A, non-B hepatitis has been carried out by the so-called "exclusion diagnosis" whose method comprises confirming increased levels of alanine aminotransferase and of aspartate aminotransferase; determining whether the hepatitis is hepatitis A, hepatitis B, or other hepatitis caused by known viruses such as CMV and EBV which can cause liver disorders; and finally diagnosing as being the non-A, non-B hepatitis if the hepatitis is other than the diseases described above. However, it is difficult to distinguish non-A, non-B hepatitis from other viral hepatitises by the exclusion diagnosis method since its clinical images are similar to those of other viral hepatitises, and to identify healthy carriers who have no abnormal ALT values. For these reasons it is hard to prevent the viral infection through transfusion of blood from healthy carriers, and therefore it is supposed that the non-A, non-B hepatitis occupies more than 90% of hepatitises. In Japan, the number of its patients reaches about one million per year.

To improve such a situation, the development of materials for diagnosing non-A, non-B hepatitis has been carried out by many researchers, but many of the developed materials had low reliability. Among the materials, a material with the highest reliability is considered to be a material developed by M. Houghton et al (PTC Patent Application No. WO 89/04669; PTC/JP90/500880) in Chiron Corporation (USA). Chiron Corporation has been making effort to clone the viral gene of interest in order to know almost the entire genome structure of hepatitis C virus (HCV, designated by Chiron Corporation), and developed a kit for diagnosis which comprises an antigenic protein obtained by expressing a part of the HCV gene.

Since then, many HCV genes specific for non-A, non-B hepatitis have been separated by immunoscreening in Japan. As a result, it has been found that HCV can be classified into: HCV Group I having highly homologous nucleotide and amino acid sequences to those of the HCV separated by Chiron Corporation; and HCV Group II having their low homologies and thus considered to be a virus different from the HCV Group I (Japanese Patent Application No. 3-189268). The kit sold by Chiron Corporation has been verified to respond at a low positive rate of 50 to 70% when tested in sera from Japanese non-A, non-B hepatitis patients. Therefore, the development of reagents for the diagnosis has been required which have a higher accuracy in epidemiological aspects.

HCV, as stated above, can be classified into Group I cloned by Chiron Corporation and Group II cloned by the present inventors, both Groups I and II being infectious pathogens of the hepatitis. Many interestings have been directed to how the two groups of HCV are clinically associated with each other in viorogical and clinical pathological aspects. On example thereof is an interferon (IFN) treatment of non-A, non-B hepatitis. IFN, which is an anti-virus agent, is believed to prevent chronic symptoms of the hepatitis by blocking a lasting infection of HCV, but it is known that the effect of an IFN treatment on progressive diseases such as chronic hepatitis and hepatic cirrhosis is as low as about 30% while its effect on acute hepatitis is high. Miyazaki et al (The 28th Congress of the Japanese Liver Society, General lecture No. 4, Abstract p. 75, 1992) has found that patients who suffer from hepatitis C and have high effect of the IFN treatment have been infected with HCV Group II, using the PCR technique.

Although the HCV gene can be amplified and detected using a small amount of infected serum by the PCR technique, this technique can not be utilized in testing many samples because its handling is complex. If an enzyme-linked immunosorbent assay (ELISA) system for screening patients infected specifically with either HCV Group I or HCV Group II is developed, it will be possible for HCV Group II-infected patients to receive an early effective IFN treatment. Such a method will also be useful for the detection of mixed infection-having patients who are infected with both the HCV Groups I and II.

SUMMARY OF THE INVENTION

Accordingly, an object of the present invention is to provide antigenic peptides for use in grouping hepatitis C virus.

Another object of the present invention is to provide a method for grouping hepatitis C virus using the peptides.

An other object of the present invention is to provide a kit for use in grouping hepatitis C virus, which comprises two antigenic peptides in combination which can react specifically with antibodies to HCV Group I and to HCV Group II, respectively.

Still another object of the present invention is to provide a method for grouping hepatitis C virus using the kit.

BRIEF DESCRIPTION OF THE DRAWINGS

FIG. 1 shows amino acid sequences of the antigenic peptides: C14-1, C14-1-2, C14-2 and C14-2-2, as well as epitope mapping for examining peptide fragments (indicated by solid lines) useful in HCV grouping, wherein star marks (*) indicate homologous amino acids between C14-1 and C14-1-2 or between C14-2 and C14-2-2.

DETAILED DESCRIPTION OF THE INVENTION

Figure 2:
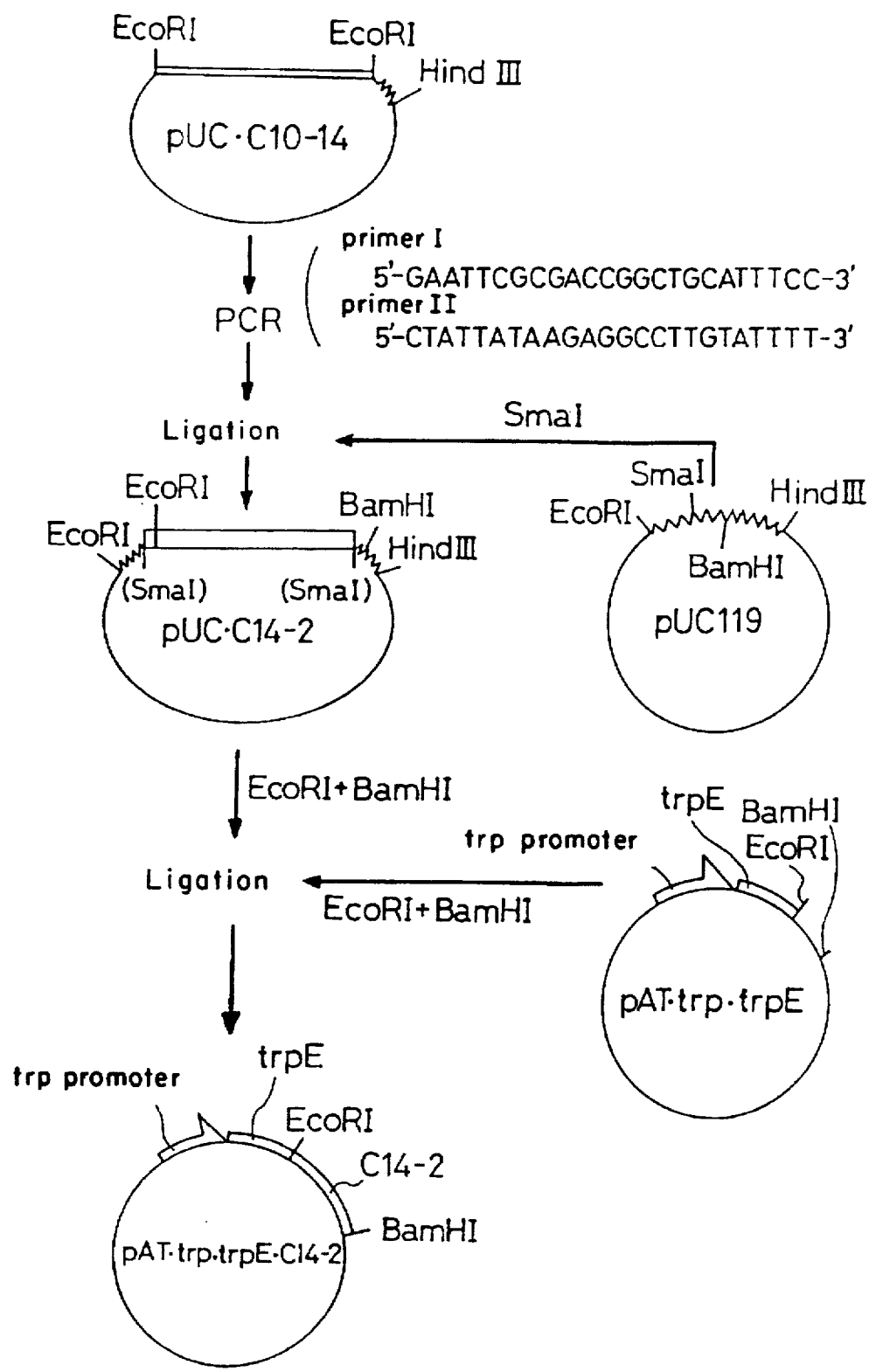
FIG. 2 shows a procedure for constructing C14-2-expression vector pAT.trp.trpE.C14-2.

As described above, hepatitis C virus (i.e., HCV) is roughly classified into Group I and Group II by comparison of homology between their amino acid sequences. The homology can be determined on the basis of comparison with HCV I (see PCT Patent Application No. WO90/11089, PCT/JP90/500880) cloned by Chiron Corporation, and thereby HCV can be classified into a group having a homology higher than about 80% and a group having a homology less than about 80%. The former is referred to as Group I and the latter as Group II. Herein, the Group I and the Group II have definitions described above. The term "grouping" as used herein means distinguishing Group I from Group II or dividing into Group I and Group II, and identifying or recognizing either Group I or Group II.

During the past several years, full length HCV clones have been isolated and their nucleotide and amino acid sequences have been determined. As a result, it has been found that the Group I can be divided into Type I and Type II while the Group II into Type III and Type IV. For example, HCV Type I is "HCV I" isolated by Chiron Corporation (see PCT Patent Application No. WO90/11089, PCT/JP90/500880), HCV Type II is "J" isolated by Shimotono et al (see Proc. Natl. Acad. Sci. USA 87, 9524–9528 (1990)), HCV Type III is "J6" isolated by Okamoto et al (see J. Gen. Virol. 72: 2697–2704 (1991)), and HCV.Type IV is "J8" isolated by Okamoto et al (see Virology 188: 331–341 (1992)). The homology based on amino acid sequences is approximately 85% between Type I and Type II or between Type III and Type IV.

The present inventors have now found that among various peptides obtained by cloning HCV genes from sera of hepatitis C patients, amplifying DNA fragments so obtained and expressing the DNA fragments in a large scale, antigenic peptides which can react specifically with sera of hepatitis C patient shaving HCV Group I or II are present. Thus, it has been found that the peptides useful in grouping the two groups are present in the region corresponding to the amino acid numbers 1674 to 1760 of the HCV I-encoded polypeptide described in PCT/JP90/500880, the peptide region being encoded by the NS4 region along HCV genome. More particularly, the found antigenic peptides useful in identifying HCV Group I are C14-1 peptide having the amino acid sequence shown in SEQ ID NO:1 and C14-1-2 peptide having the amino acid sequence shown in SEQ ID NO:2, the latter peptide being related to the C14-1 peptide; and the found antigenic peptides useful in identifying HCV Group II are C14-2 peptide having the amino acid sequence shown in SEQ ID NO:3 and C14-2-2 peptide having the amino acid sequence shown in SEQ ID NO:4, the latter peptide being related to the C14-2 peptide. These sequences also correspond to the region of amino acid numbers 1680 to 1764 of the polypeptides encoded by J6 and J8 genomes isolated by Okamoto et al (Okamoto et al., supra). In the grouping, other useful peptides may be fragments of the four peptides described above.

Accordingly, the present invention provides an antigenic peptide having an amino acid sequence or partial sequence thereof shown in SEQ ID NO:1 or SEQ ID NO:2 and capable of reacting specifically with antibodies directed against Group I of hepatitis C virus; and an antigenic peptide having an amino acid sequence or partial sequence thereof shown in SEQ ID NO:3 or SEQ ID NO:4 and capable of reacting specifically with antibodies directed against Group II of hepatitis C virus.

HCV in specimens (e.g., blood) can be classified into either HCV Group I or HCV Group II using the above-mentioned peptides as antigens.

According to the present invention, the two antigenic peptides capable of reacting specifically with antibodies to HCV Groups I and II respectively may be combined to form a kit, and such a kit will be useful in detecting mixed infection-having patients who have been infected with both HCV Groups I and II.

Thus, the present invention provides a kit for identifying Group I or Group II of hepatitis C virus, which comprises in its separate sections at least one first antigenic peptide selected from the group consisting of peptides having amino acid sequences or partial sequences thereof shown in SEQ ID NO:1 and SEQ ID NO:2 and capable of reacting specifically with antibodies directed against Group I of hepatitis C virus, and variants of the peptides which have the same function as the peptides; and at least one second antigenic peptide selected from the group consisting of peptides having amino acid sequences or partial sequences thereof shown in SEQ ID NO:3 and SEQ ID NO:4 and capable of reacting specifically with antibodies directed against Group II of hepatitis C virus, and variants of the peptides which have the same function as the peptides.

The term "variants of the peptides which have the same function" as used herein refers to peptides having at least one different amino acid substituted for the constituent amino acids in the amino acid sequence or its partial sequence shown in SEQ ID NO:1, 2, 3 or 4, provided that the variant can be react specifically with antibodies to the HCV Group I or II defined above. As can be seen from the comparison between C14-1 and C14-1-2 or between C14-2 and C14-2-2 in FIG. 1, examples of the substitution of amino acids include substitutions between amino acids having similar chemical properties such as Ile-Val, Leu-Ile, Val-Ala, Met-Ile, Lys-Arg, Asp-Gln, and the like.

The antigenic peptides as used in the present invention may be fused with an other inert peptide which does not affect the antigen-antibody reaction with the viral antibodies, or they may be modified chemically (e.g., acylation of N-terminus of the peptides). Further examples of the antigenic peptides are anti-idiotype antibodies thereof.

Examples of the useful peptide fragments, but not limited to the below, include fragments having the following sequences of: amino acid positions 20 to 44 (designated as "1-Y" in FIG. 1), 37 to 62 (1-Z) or a combination thereof in the amino acid sequence shown in SEQ ID NO:1; amino acid positions 20 to 44 (1-Y), 37 to 62 (1-Z), 53 to 74 (1-B), 64–87 (1-A) or combinations thereof in the amino acid sequence shown in SEQ ID NO:2; amino acid positions 20 to 44 (2-Y), 37 to 62 (2-Z) or a combination thereof in the amino acid sequence shown in SEQ ID NO:3; and amino acid positions 20 to 44 (2-Y), 37 to 62 (2-Z), 53 to 74 (2-B), 64–87 (2-A) or combinations thereof in the amino acid sequence shown in SEQ ID NO:4. Herein, the term "combination(s)" means a binding of at least two fragment sequences such as sequences 20–62, 20–74 or the like.

The antigenic peptides can be prepared by means of recombinant DNA techniques or peptide synthesis techniques.

The process for preparing the antigenic peptides by the conventional recombinant DNA techniques comprises the following steps of:

constructing a replicable expression vector carrying a DNA fragment coding for a peptide which has an amino acid sequence of its partial sequence shown in SEQ ID NO:1, 2, 3 or 4;

incorporating the expression vector in a host cell to obtain a transformed cell;

culturing the transformed cell under conditions suitable for expression of the DNA fragment; and recovering the peptide of interest.

The following is an example of construction of the expression vector: A DNA fragment coding for the peptide of interest is ligated to a conventional plasmid (e.g., pUC119) and then amplified. After the resulting plasmid is digested doubly with two restriction endonucleases, the DNA fragment obtained is separated and purified using agarose gel electrophoresis. On the other hand, an appropriate expression vector such as pAT.trp.trpE (see JP-A-1-215,289) is digested with the same endonucleases and then the vector fragment obtained is purified in the similar manner. The ligation of the vector fragment with the above-mentioned DNA fragment results in a desired expression vector in which an HCV Group I or II-specific antigen can be expressed (see Examples set forth below).

Usable promoters for expression may be ones from Escherichia coli, phages, viruses and the like, such as tryptophane synthetase operon (trp) promoter, lactose operon (lac) promoter, lambda phage $P_L$ or $P_R$ promoter, alcohol dehydrogenase promoter, and SV40 promoter. In the expression vector DNA, the following may be present: a selection marker sequence such as antibiotic resistance gene; an origin of replication; a transcription termination factor; a ribosome binding site; and the like.

Examples of usable host cells for transformation include general microorganisms such as E. coli, Bacillus subtilis and yeast; insect cells; plant cells; and mammalian cells. The preferred host cell is a prokaryote, particularly E. coli. The transformation can be carried out by the conventional methods for incorporating an expression vector in a host cell. When a bacterial cell (e.g., E. coli) is used as a host cell, a direct incorporation method is advantageous in which rubidium chloride (Hanahan, DNA cloning: A practical approach, IRC Press (1985)) or calcium chloride (Mandel, M. and Higa, A. J. Mol. Biol., 53: 159–162 (1970)) is used. When a higher organism cell is used as a host cell, an incorporation method using an viral vector is advantageous.

Next, the host cell carrying an expression vector is cultured in an appropriate medium to produce a desired peptide. Purification of the desired peptide from the host cells may be carried out as follows: Following the disruption of the host cells by sonication, the insoluble fraction which contains a peptide encoded by hepatitis C virus cDNA or its fused peptide with an other peptide (e.g., trpE) is separated by centrifugation, and the recombinant peptide is solubilized from the fraction with an urea-containing buffer and then partially purified by subjecting it to ion-exchange column chromatography (e.g., Q-Sepharose). To further purify the recombinant peptide, a procedure such as gel filtration (e.g., HiLoad Superdex) may be used.

Alternatively, the peptides of the present invention may be prepared by the conventional peptide synthesis techniques which include both a liquid phase method and a solid phase method (see Lectures on Biochemical Experiments I, "Protein Chemistry IV: Chemical modifications and Peptide syntheses", pp. 207–495, 1977, by the Japanese Biochemical Society). In general, if the desired peptide is a long peptide, small peptides composed of about 5 to 10 amino acids can first be synthesized on a synthetic resin phase and linked to each other sequentially or in a step wise way, and the desired peptide can be obtained following deprotection.

The peptides of the present invention prepared by the methods described above, in general, are stored in the form of a solid in a dark cold room after its drying under vacuum or lyophilization. When packaged in the form of a kit, the antigenic peptide specific for HCV Group I antibodies and the antigenic peptidespecific for HCV Group II antibodies are individually placed in separate sections of the kit. Examples of such a section are capped vials and ampoules made from glass or resin, microtiterplates and the like. The preferred section is of that each of the peptides adsorbed (or bound) onto microtiterplate wells for ELISA can be stabilized by such a suitable procedure (lyophilization) that the peptides can maintain a binding ability to HCV antibodies. In place of the microtiterplate, tubes, beads and supports (e.g., erythrocytes) for aggregation may be used. In the kit of the present invention, the following reagents needed for immunological analyses may optionally be comprised: a buffer; an enzyme-labeled or radioactively labeled second antibody; a color development agent; stop agent for immunological reaction; and the like.

Tables 1 to 4 show the EIA results of the immunological reactions of the polypeptide: trpE.C14-1, trpE.C14-1-2, trpE.C14-2, trpE.C14-2-1 (consisting of amino acid residues 23 to 63 in SEQ ID NO:3) or trpE.C14-2-2 with sera from patients who have been diagnosed clinically as hepatitis C. The results indicate that the trpE.C14-1 and trpE.C14-1-2 can specifically identify HCV Group I while the trpE.C14-2, trpE.C14-2-1 and trpE.C14-2-2 can specifically identify HCV Group II.

Tables 5, 6 and 7 show the EIA results of the immunological reactions of the peptide fragments of the present invention capable of reacting specifically with HCV Group I or II, with various sera from hepatitis C-having patients. The results of Tables 5, 6 and 7 show that the patients have been infected with HCV Group I alone, or with HCV Group II alone, or with both HCV Groups I and II. A commercially available diagnosis reagent for hepatitis C, Immucheck-HCV (ex International Reagents Corporation, Hyogo, Japan), as a comparative reagent could not distinguish HCV.Group I from HCV Group II.

Therefore, the present invention provides a method for grouping hepatitis C virus, which comprises:

contacting an antigenic peptide having the amino acid sequence or its partial sequence shown in SEQ ID NO:1 or SEQ ID NO:2, with a specimen presumed to contain antibodies directed against HCV in order to carry out an immunological reaction; and detecting antibodies directed against HCV belonging to Group I as positive.

When an antigenic peptide having the amino acid sequence or its partial sequence shown in SEQ ID NO: 3 or SEQ ID NO:4 is used, antibodies directed against HCV Group II can be detected as positive, and thus this grouping method is also included within the scope of the present invention.

The present invention further relates to use of the kit as defined above. Thus, the present invention provides a method for grouping hepatitis C virus, which comprises:

contacting at least one first peptide selected from the group consisting of peptides having amino acid sequences or partial sequences thereof shown in SEQ ID NO:1 and SEQ ID NO:2 and capable of reacting specifically with antibodies directed against Group I of hepatitis C virus, and variants of the peptides which have the same function as the peptides, and at least one second peptide selected from the group consisting of peptides having amino acid sequences or partial sequences thereof shown in SEQ ID NO:3 and SEQ ID NO:4 and capable of reacting specifically with antibodies directed against Group II of hepatitis C virus, and variants of the peptides which have the same function as the peptides, individually with a specimen presumed to contain antibodies to hepatitis C virus so as to determine the antibodies quantitatively or qualitatively by immunological reaction, the first and second peptides being included in the kit as defined above; and detecting the antibodies to Group I or Group II of hepatitis C virus.

Usable immunological assays are appropriate techniques as used conventionally in the art, for example, western blot analysis, enzyme immunoassay, immunoprecipitation, and radioisotopeimmunoassay. The conditions for measurement may appropriately be selected depending on types of the assays to be used (see Examples set forth below). The specimen is commonly blood, particularly serum.

The present invention will be illustrated by the following non-limited examples in more detail.

EXAMPLE 1

Construction of C14-1 and C14-1-2 Expression Plasmids

Cloning of HCV Antigen-Encoding DNA by the RT-PCR Method

In order to clone HCV genes from chronic hepatitis C patient's sera, the RT (reverse transcriptase)-PCR technique was used in which the cloning can be carried out using only a small amount of plasma.

To 100 μl of a hepatitis C patient's serum were first added and stirred 200 μl of 6M GTC solution (6M guanidine thiocyanate, 37.5 mM sodium citrate, 0.75% sarkosyl, 0.2M β-mercaptoethanol) and 1 μl of yeast t-RNA (10 mg/ml). To the mixture obtained, 20 μl of 3M sodium acetate (pH 5.2), 30 μl of TE-saturated phenol (pH 7.5–8.0) and 70 μl of chloroform/isoamyl alcohol (49:1) were quickly added, stirred for 10 sec, and left to stand on ice for 15 min. After centrifugation at 15,000 rpm at 4° C. for 20 min, the aqueous layer was removed, mixed with an equal volume of isopropyl alcohol, and left to stand at –20° C. for at least 1 hr. After further centrifugation under the same conditions, pellet was recovered which was then dissolved in 100 μl of 4M GTC (dilution of 6M GTC with sterilized water), mixed with an equal volume of isopropyl alcohol and left to stand at –20° C. for at least 1 hr. After centrifugation at 15,000 rpm at 4° C. for 20 min, RNA pellet was recovered, washed with 70% ethanol (1 ml), air-dried at room temperature, and dissolved in 10 μl of sterilized water. This RNA solution was used later.

HCV cDNA synthesis was carried out as follows: Ten μl of the RNA solution was placed in a silicone-treated tube (0.5 ml), heated at 70° C. for 3 min, and quickly chilled on ice. Then, to the solution were added 1 μl of RNase inhibitor (50 units/μl; ex Takara Shuzo), 1 μl of dNTPs (20 mM each), 100 mM DTT, 4 μl of 5×RT buffer (250 mM Tris-HCl (pH 8.5), 375 mM KCl, 15 mM MgCl$_2$), 1 μl of random oligohexamer primer (100 pmol/μl) and reverse transcryptase (BRL) (200 units/μl), and sterilized water was added to the mixture to a total volume of 20 μl. HCV cDNA synthesis was carried out at 42° C. for 2 hr. The reaction mixture was then heated at 94° C. for 5 min to inactivate the enzyme.

PCR was carried out using the obtained cDNA as follows: The PCR used was a two step method in which a first step PCR is first performed using two primers and then a second step PCR is performed using two primers present inside the DNA sequences of the first PCR products. By this method, both amplification sensitivity and specification of detected DNA can be raised.

To amplify C14-1 region, the following primers were synthesized with reference to the known sequence (Proc. Natl. Acad. Sci. USA 87, 9524–9528, 1990):

primers used in the 1st PCR:

5S1: 5'-AGGTCGTCACTAGCACCTGGGTGC-3' (SEQ ID NO:10); and

5A1: 5'-TGTATCCCGCTGATGAAGTTCCAC-3' (SEQ ID NO:11);

primers used in the 2nd PCR:

5S2: 5'-GAATTCACGACAGGCAGCGTGGTC-3' (SEQ ID NO:12); and

5A2: 5'-CTATTACAGCAATCCGAGCGCCCT-3' (SEQ ID NO:13).

In a 0.5-ml tube, 20 μl of the reaction solution for cDNA synthesis, 8 μl of 10×PCR buffer (100 mM Tris-HCl (pH 8.3), 500 mM KCl, 15 mM MgCl$_2$, 0.1% gelatine), the two 1st step primers (75 pmoles each) and 8 μl of 2 mM dNTPs were placed and then sterilized water was added to the mixture to a total volume of 100 μl. After heating at 94° C. for 10 min, 1 μl of AmpliTaq (5 units; ex Perkin-Elmer-Cetus) was added to the mixture with stirring and mineral oil was further overlaid on the mixture solution prior to brief centrifugation. The conditions of PCR were: denaturation, 94° C. for 1 min; annealing, 55° C. for 1 min; extension, 72° C., 2 min; and 30 cycles. In a fresh 0.5-ml tube, 10 μl of the PCR reaction mixture, 9 μl of 10×PCR buffer, the two 2nd step PCR primers (75 pmoles each) and 9 μl of 1 mM dNTPs were placed and sterilized water was added to the mixture to a total volume of 100 μl. After heating at 94° C. for 10 min, 1 μl of AmpliTaq (5 units) was added to the mixture with stirring and mineral oil was overlaid on the mixture solution prior to brief centrifugation. Second PCR was carried out under the same conditions as in the first PCR. Following the reaction, 10 μl of the reaction mixture was analyzed by agarose gel electrophoresis, by which a specifically amplified DNA fragment could be detected.

The C14-1 DNA fragment (about 200 bp) which has been amplified by PCR was separated by low-melting point agarose gel electrophoresis, and the gel containing the DNA fragment was dissolved in 200 μl of sterilized water at 68° C. for 15 min. The solution was extracted twice with TE buffer (10 mM Tris-HCl (pH 8.0), 1 mM EDTA)-saturated phenol to separate an aqueous layer containing the DNA fragment. The aqueous layer was subjected to ethanol precipitation to yield precipitates of DNA to which 2 μl of 10×kinase buffer (0.5M Tris-HCl, pH 7.6, 0.1M MgCl$_2$, 50 mM DTT, 1 mM spermidine, 1 mM EDTA pH 8.0), 1 μl of 10 mM ATP and 1 μl of T4 kinase (10 units/μl; ex Takara Shuzo) were then added and subsequently sterilized water was added thereto to a total volume of 20 μl. The mixture was allowed to react at 37° C. for 1 hr for phosphorylation of the 5' end. After the kinase was inactivated by heating at 68° C. for 10 min, the reaction mixture was subjected to ligation with pUC119 (Vieira, J. and Messing, J., Methods in Enzymology, 153, 3–11 (1987)). The pUC119 (1 μg) was previously digested in 20 μl of restriction reaction solution (10 mM Tris-HCl pH 8.0, 7 mM MgCl$_2$, 20 mM KCl, 10 units of SmaI enzyme (ex Takara Shuzo)) at 37° C. for 1 hr, and the reaction mixture was then heated at 68° C. for 10 min to obtain an SmaI cloning vector solution after addition of 80 μl of sterilized water. The ligation reaction of 10 μl of the phosphorylated DNA fragment with 2 μl of the SmaI vector was carried out in 2 μl of 10×buffer (0.66M Tris-HCl pH 7.6, 50 mM MgCl$_2$, 50 mM DTT), 1 μl of 10 mM ATT, 1 μl of T4 ligase (350 units/μl; ex Takara Shuzo) and 4 μl of sterilized water at 16° C. overnight.

Ten μl of the ligation reaction mixture was transformed into *Escherichia coli* strain JM109. The compitent *E. coli* strain has previously been made by the calcium chloride method (Mandel, M. and Higa, A., J. Mol. Biol. 53, 159–162 (1970)).

The transformed *E. coli* was then cultured at 37° C. overnight on LB-Amp plate (1% tryptone, 0.5% yeast extract, 0.5% NaCl, 1.5% agar, ampicillin (25 μg/ml)) to which 50 μl of 2% X-Gal (5-bromo-4-chloro-3-indolyl-β-D-galactopyranoside) was applied together with 10 μl of 100 mM IPTG (isopropyl-β-D-thiogalactopyranoside). One platinum loop of white colony generated on the plate was picked up and cultured in LB medium (1% tryptone, 0.5% yeast extract, 0.5% NaCl) containing 25 μg/ml of ampicillin at 37° C. overnight with shaking. 1.5 ml of the culture was centrifuged to collect the bacterial cells which were subjected to mini-preparation in accordance with the alkaline method (Maniatis et al., Molecular Cloning: A Laboratory Manual, 1982) in order to obtain a plasmid DNA. One μg of the obtained plasmid DNA was digested at 37° C. for 1 hr in 30 μl of restriction reaction solution (100 mM Tris-HCl pH 7.5, 50 mM NaCl, 7 mM MgCl$_2$, 10 units each of EcoRI and HindIII (ex Takara Shuzo)), and the digest was subjected to size analysis by agarose gel electrophoresis to confirm an about 250 bp insert DNA fragment. The clone containing the insert DNA fragment was named pUC.C14-1. The C14-1 DNA fragment was sequenced for nucleotide sequence by Sanger's dideoxy chain termination procedure (Sanger, F., Science, 214, 1205–1210 (1981)), by which its deduced amino acid sequence was also determined. The determined amino acid and nucleotide sequences are shown in SEQ ID NOs: 1 and 5, respectively.

In order to isolate a genomic HCV RNA region (named C6-2) of from the latter half of NS3 to the first half of NS5, RT-PCR was carried out in the same manner as above excepting use of the following primers:

primers used in a first PCR:

KK1: 5'-GGCTATACCGGTGACTTTGA-3' (SEQ ID NO:14); and
A6: 5'-GTCTCAGCTCCCTTCCGATC-3' (SEQ ID NO:15);

primers used in a second PCR:

KK5: 5'-GATCTACTGCTAACACATGTGTCA-3' (SEQ ID NO:16); and
A6: (see above).

After reaction, the amplified fragment was recovered, and then inserted into pBM vector (see below) in the above-described manner to produce C6-2.

One ng of C6-2 as template was mixed with 50 pmol each of primers (5'-GCGAATTCACAACAGGCAGTGTGGTCATT-3' (SEQ ID NO:17) and 5'-GCTCATTAGAAGGTCTCAAGGGCTCGCCA-3' (SEQ ID NO:18)), 67 mM Tris-HCl (pH8.8), 16.6 mM (NH$_4$)$_2$SO$_4$, 0.2 mM dNTPs, 2 mM MgCl$_2$, 0.2 mg/ml gelatine, and 0.05% Triton X-100 in a total volume of 50 μl, and 2.5 units of Taq DNA polymerase was further added to the mixture. Following overlay of paraffin oil, PCR of the C6-2 fragment was undergone (94° C. for 30 sec, 55° C. for 60 sec, 72° C. for 120 sec, 30 cycles). The reaction mixture was subjected to agarose gel electrophoresis to isolate an approximately 260 bp fragment which was subsequently recovered into 50 μl of TE buffer (10 mM Tris-HCl (pH 7.5), 1 mM EDTA) by the Glass powder method (Gene Clean II; ex BIO101). To the recovered DNA solution (25 μl) were added 3 μl of 10×T4 buffer (0.5M Tris-HCl (pH 7.5), 100 mM MgCl$_2$, 100 mM DTT), 3 μl of 2 mM dNTPs, and 3 μl of ATP, and then 5 units of DNA polymerase I (ex New England Biolab) and 10 units of T4 polynucleotidyl kinase (ex Takara Shuzo) were further added to the mixture in order to allow to react at 37° C. for 1 hr. Desired DNA fragment was recovered into 25 μl of TE solution by the Glass powder method.

On the other hand, 1 μg of pT7T3 19U (ex Pharmacia) was cleaved by restriction reaction in 20 μl of restriction system (10 mM Tris-HCl (pH 8.0), 7 mM MgCl$_2$, 20 mM KCl, 10 units of SmaI) at 37° C. for 1 hr. To the reaction mixture were added 10 μl of 1M Tris-HCl (pH 8.0), 70 μl of sterilized water and 2 units of Bacterial alkaline phosphatase (ex Takara Shuzo) in order to allow to react at 68° C. for 30 min. Following the reaction, DNA in the solution was extracted with a phenol/chloroform mixed solution and then precipitated with ethanol. After the recovered DNA (10 μl) was dissolved in 10 ml of the TE buffer, 1 μl of the solution was mixed with 10 μl of the above-described PCR DNA fragment to which 50 μl of Ligation liquid A and 10 μl of Ligation liquid B (DNA Ligation Kit; ex Takara Shuzo) were then added and mixed well in order to allow to react 16° C. for 1 hr. Ten μl of the obtained DNA solution was transformed into *E. coli* strain XL1-blue (ex Stratagene) in accordance with the Hanahan's method (DNA cloning: A practical approach (ed. by D. M. Glover), vol. 1, p. 109, IRC Press (1985)). The resulting clone was of that the plasmid DNA from the transformed cells could be cleaved with EcoRI and SalI to produce an about 290 bp fragment. It has been found that the isolated DNA fragment has the nucleotide sequence shown in SEQ ID NO:6 and codes for the peptide (i.e., C14-1-2) having the amino acid sequence shown in SEQ ID NO:2.

Construction of Expression Vector

One μl of the pUC.C14-1 DNA was digested in 20 μl of restriction solution (100 mM Tris-HCl (pH 7.5), 50 mM NaCl, 7 mM MgCl$_2$, 10 units each of EcoRI and BamHI (ex Takara Shuzo)) at 37° C. for 1 hr and subjected to low-melting point agarose gel electrophoresis so as to prepare an about 200 bp purified DNA fragment. On the other hand, one μg of the expression vector pAT.trp.trpE DNA (JP-A-1-215, 289) was treated under the same conditions to obtain a vector DNA fragment. The resulting EcoRI-BamHI treated vector DNA (1 μg) was ligated with the C14-1 DNA fragment prepared above in 5 μl of 10×ligase buffer (660 mM Tris-HCl (pH 7.5), 66 mM MgCl$_2$, 100 mM dithiothreitol (DTT), 10 mM ATP) containing 350 units of T4 ligase (ex Takara Shuzo) plus water in a total volume of 50 μl at 16° C. overnight.

Ten μl of the reaction mixture obtained was transformed into *Eschericia coli* strain C600. The competent *E. coli* strain for transformation has been made by the calcium chloride (Mandel, M. and Higa, A. J. Mol. Biol. 53, 159–162 (1970)). The transformed cells was plated on LB-plate (1% tryptone, 0.5% yeast extract, 0.5% NaCl, 1.5% agar) containing 25 μg/ml of ampicillin, and stored at 37° C. overnight. One platinum loop of colony generated on the plate was picked up and cultured in the LB medium containing 25 μg/ml ampicillin at 37° C. overnight. The obtained culture (1.5 ml) was centrifuged to collect bacterial cells and subjected to mini-preparation of plasmid DNA by the alkaline lysis method (Maniatis et al., supra).

The resulting DNA (1 μg) was doubly digested with EcoRI and BamHI, and in the digests the expression plasmid pAT.trp.trpE C14-1 was screened from which an about 200 bp EcoRI-BamHI fragment can be obtained.

In the similar way, the expression plasmid pAT.trp.trpE C14-1-2 from which an about 290 bp EcoRI-SalI fragment can be obtained could be constructed from pUC.C14-1-2 DNA.

EXAMPLE 2

Construction of C14-2 Expression Vector

Cloning of HCV Antigen-Encoding DNA

PCR of clone C10-14 (FERM P-3436; Japanese Patent Application No. 3-189,268) which is considered to be an HCV Group II was carried out using the PCR primers: 5'-GAATTCGCGACCGGCTGCATTTCC-3' (SEQ ID NO:19) and 5'-CTATTATAAGAGGCCTTGTATTTT-3' (SEQ ID NO:20) as follows. C10-14 clone DNA (1 ng) was added to 10 µl of 10×PCR buffer (0.1M Tris-HCl (pH 8.3), 0.5M KCl), the two primers (75 pmol each) and 10 µl of 2 mM dNTPs, and to the mixture was further added sterilized water to total volume of 100 µl. After heating at 94° C. for 10 min, 1 µl of Ampli Taq (5 units/µl; ex Perkin-Elmer-cetus) was added to the mixture, followed by overlay of two drops of mineral oil onto the mixture. The PCR conditions were: denaturation, 94° C. for 1 min; annealing, 55° C. for 1 min; extension, 72° C. for 2 min; and 30 cycles.

The PCR-amplified C14-2 fragment (about 200 bp) was separated by low-melting point agarose gel electrophoresis, and the gel containing the DNA fragment was dissolved in 200 µl of sterilized water at 68° C. for 15 min. The solution was extracted twice with TE buffer (10 mM Tris-HCl (pH 8.0), 1 mM EDTA)-saturated phenol to separate an aqueous layer containing the DNA fragment. The aqueous layer was subjected to ethanol precipitation to yield precipitates of DNA fragment to which 2 µl of 10×kinase buffer (0.5M Tris-HCl, pH 7.6, 0.1M MgCl$_2$, 50 mM DTT, 1 mM spermidine, 1 mM EDTA pH 8.0), 1 µl of 10 mM ATP and 1 µl of T4 kinase (10 units/µl; ex Takara Shuzo) were then added and subsequently sterilized water was added thereto to total volume of 20 µl. The mixture was allowed to react at 37° C. for 1 hr for phosphorylation of the 5' end. After the kinase was inactivated by heating at 68° C. for 10 min, the reaction mixture was subjected to ligation with pUC119 (Vieira, J. and Messing, J., Methods in Enzymology, 153, 3–11 (1987)). The pUC119 (1 µg) was previously digested in 20 µl of restriction reaction solution (10 mM Tris-HCl pH 8.0, 7 mM MgCl$_2$, 20 mM KCl, 10 units of SmaI enzyme (ex Takara Shuzo)) at 37° C. for 1 hr, and the reaction mixture was then heated at 68° C. for 10 min to obtain an SmaI cloning vector solution after addition of 80 µl of sterilized water. The ligation reaction of 10 µl of the phosphorylated DNA fragment with 2 µl of the SmaI vector was carried out in 2 µl of 10×buffer (0.66M Tris-HCl pH 7.6, 50 mM MgCl$_2$, 50 mM DTT), 1 µl of 10 mM ATT, 1 µl of T4 ligase (350 units/µl; ex Takara Shuzo) and 4 µl of sterilized water at 16° C. overnight.

Ten µl of the ligation reaction mixture was transformed into *Escherichia coli* strain JM109. The compitent *E. coli* strain has previously been made by the calcium chloride method (Mandel, M. and Higa, A., J. Mol. Biol. 53, 159–162 (1970)).

The transformed *E. coli* was then cultured at 37° C. overnight on LB-Amp plate (1% tryptone, 0.5% yeast extract, 0.5% NaCl, 1.5% agar, ampicillin (25 µg/ml)) to which 50 µl of 2% X-Gal (5-bromo-4-chloro-3-indolyl-β-D-galactopyranoside) were applied together with 10 µl of 100 mM IPTG (isopropyl-β-D-thiogalactopyranoside). One platinum loop of white colonies generated on the plate was picked up and cultured in LB medium (1% tryptone, 0.5% yeast extract, 0.5% NaCl) containing 25 µg/ml of ampicillin at 37° C. overnight with shaking. 1.5 ml of the culture was centrifuged to collect the bacterial cells which were subjected to mini-preparation in accordance with the alkaline lysis method (Maniatis et al., supra) in order to obtain a plasmid DNA. One µg of the obtained plasmid DNA was digested at 37° C. for 1 hr in 30 µl of restriction reaction solution (100 mM Tris-HCl pH 7.5, 50 mM NaCl, 7 mM MgCl$_2$, 10 units each of EcoRI and HindIII (ex Takara Shuzo)), and the digest was subjected to size analysis by agarose gel electrophoresis to confirm an about 250 bp insert DNA fragment. The clone containing the insert DNA fragment was named pUC.C14-2. The C14-2 DNA fragment was sequenced for nucleotide sequence by Sanger's dideoxy chain termination procedure (Sanger, F., supra), by which its deduced amino acid sequence was also determined. The determined amino acid and nucleotide sequence are shown in SEQ ID NOs: 3 and 7, respectively.

By repeating the above-described cloning procedures except that 5'-GAATTCCCTGATAAGGAAATTTTA-3' (SEQ ID NO:21) and 5'-CTATTATAAGAGGCCTTGTATTTT-3' (SEQ ID NO:22) were used as PCR primers, a clone containing about 140 bp C14-2-1 DNA fragment was prepared which was named pUC.C14-2-1. The C14-2-1 DNA fragment codes for the peptide having the sequence of positions 23 to 63 in the amino acid sequence shown in SEQ ID NO:3.

Construction of Expression Plasmid

In the similar way to that in Example 1, the expression plasmid pAT.trp.trpE.C14-2 from which an about 200 bp EcoRI-BamHI DNA fragment can be prepared was constructed using the pUC.C14-2 DNA as a starting material. The strategy for the construction is shown in FIG. 2. Expression plasmid pAT.trp.trpE.C14-2-1 was also constructed from the pUC.C14-2-1 DNA in the similar manner.

EXAMPLE 3

Construction of C14-2-2 Expression Plasmid

Cloning of HCV Antigen-Encoding DNA

In order to clone HCV genes from chronic hepatitis C patient's sera, the RT-PCR technique was used.

To 100 µl of a hepatitis C patient's serum were first added and stirred 200 µl of 6M GTC solution (6M guanidine thiocyanate, 37.5 mM sodium citrate, 0.75% sarkosyl, 0.2M β-mercaptoethanol) and 1 µl of yeast t-RNA (10 mg/ml). To the mixture obtained, 20 µl of 3M sodium acetate (pH 5.2), 30 µl of TE-saturated phenol (pH 7.5–8.0) and 70 µl of chloroform/isoamyl alcohol (49:1) were quickly added, stirred for 10 sec, and left to stand on ice for 15 min. After centrifugation at 15,000 rpm at 4° C. for 20 min, the aqueous layer was removed, mixed with an equal volume of isopropyl alcohol, and left to stand at −20° C. for at least 1 hr. After again centrifugation under the same conditions, a precipitation was recovered which was then dissolved in 100 µl of 4M GTC (dilution of 6M GTC with sterilized water), mixed with an equal volume of isopropyl alcohol and left to stand at −20° C. for at least 1 hr. After centrifugation at 15,000 rpm at 4° C. for 20 min, an RNA pellet was recovered, washed with 70% ethanol (1 ml), air-dried at room temperature, and dissolved in 10 µl of sterilized water. This RNA solution was used later.

HCV cDNA synthesis was carried out as follows: Ten μl of the RNA solution was placed in a silicone-treated tube (0.5 ml), heated at 70° C. for 3 min, and quickly chilled on ice. Then, to the solution were added 1 μl of RNase inhibitor (50 units/μl; ex Takara Shuzo), 1 μl of dNTPs (20 mM each), 100 mM DTT, 4 μl of 5×RT buffer (250 mM Tris-HCl (pH 8.5), 375 mM KCl, 15 mM MgCl$_2$), 1 μl of random oligohexamer primer (100 pmol/μl) and reverse transcriptase (BRL) (200 units/μl), and sterilized water was added to the mixture to a total volume of 20 μl. HCV cDNA synthesis was carried out at 42° C. for 2 hr. The reaction mixture was then heated at 94° C. for 5 min to inactivate the enzyme.

PCR was carried out using the two step method as defined in Example 1.

To amplify HCV NS4 region containing the C14-2-2 region, the following primers were synthesized with reference to the known sequence (J. Gen. Virol. 72: 2697–2704 (1991)):

primers used in the 1st PCR:

5'-GGATCACCGGTGACTTTGA-3' (SEQ ID NO:23); and
5'-CCCCAAAATGTTGAGAAGGATA-3' (SEQ ID NO:24);

primers used in the 2nd PCR:

5'-GATGCCCACTTCCTCTCCCA-3' (SEQ ID NO:25); and
5'-GTGCTAGTTGACAACGGACTGGT-3' (SEQ ID NO:26).

In a 0.5-ml tube, 20 μl of the reaction solution for cDNA synthesis, 8 μl of 10×PCR buffer (100 mM Tris-HCl (pH 8.3), 500 mM KCl, 15 mM MgCl$_2$, 0.1% gelatine), the two 1st step primers (75 pmol each) and 8 μl of 2 mM dNTPs were placed and then sterilized water was added to the mixture to a total volume of 100 μl. After heating at 94° C. for 10 min, 1 μl of AmpliTaq (5 units; ex Perkin-Elmer-Cetus) was added to the mixture with stirring and mineral oil was further overlaid on the mixture solution prior to rough centrifugation. The conditions of PCR were: denaturation, 94° C. for 1 min; annealing, 55° C. for 1 min; extension, 72° C., 2 min; and 30 cycles. In a fresh 0.5-ml tube, 10 μl of the PCR reaction mixture, 9 μl of 10×PCR buffer, the two 2nd step PCR primers (75 pmol each) and 9 μl of 1 mM dNTPs were placed and sterilized water was added to the mixture to a total volume of 100 μl. After heating at 94° C. for 10 min, 1 μl of AmpliTaq (5 units) was added to the mixture with stirring and mineral oil was then overlaid on the mixture solution prior to rough centrifugation. Second PCR was carried out under the same conditions as in the first PCR. Following the reaction, 10 μl of the reaction mixture was analyzed by agarose gel electrophoresis, by which a specifically amplified DNA fragment could be detected.

The C14-8 DNA fragment (about 700 bp) which has been amplified by PCR was separated by low-melting point agarose gel electrophoresis, and the gel containing the DNA fragment was dissolved in 200 μl of sterilized water at 68° C. for 15 min. The solution was extracted twice with TE buffer (10 mM Tris-HCl (pH 8.0), 1 mM EDTA)-saturated phenol to separate an aqueous layer containing the DNA fragment. The aqueous layer was subjected to ethanol precipitation to afford a DNA fragment precipitation to which 2 μl of 10×kinase buffer (0.5M Tris-HCl, pH 7.6, 0.1M MgCl$_2$, 50 mM DTT, 1 mM spermidine, 1 mM EDTA pH 8.0), 1 μl of 10 mM ATP and 1 μl of T4 kinase (10 units/μl; ex Takara Shuzo) were then added and subsequently sterilized water was added thereto to a total volume of 20 μl. The mixture was allowed to react at 37° C. for 1 hr for phosphorylation of the 5' end. After the kinase was inactivated by heating at 68° C. for 10 min, the reaction mixture was subjected to ligation with pBM (see below; Japanese Patent Application No. 4-207,391 filed Jul. 10, 1992). The pBM (1 μg) was previously digested in 20 μl of restriction reaction solution (10 mM Tris-HCl pH 8.0, 7 mM MgCl$_2$, 20 mM KCl, 10 units of SmaI enzyme (ex Takara Shuzo)) at 37° C. for 1 hr, and the reaction mixture was then heated at 68° C. for 10 min to obtain an SmaI cloning vector solution after addition of 80 μl of sterilized water. The ligation reaction of 10 μl of the phosphorylated DNA fragment with 2 μl of the SmaI vector was carried out in 2 μl of 10×buffer (0.66M Tris-HCl pH 7.6, 50 mM MgCl$_2$, 50 mM DTT), 1 μl of 10 mM ATT, 1 μl of T4 ligase (350 units/μl; ex Takara Shuzo) and 4 μl of sterilized water at 16° C. overnight.

The pBM vector can be constructed as follows: The EcoRV-BalI sequence (1259 bp) is deleted from pBR322 (Sutchliffe, J. G., Cold Spring Harbor Symposium, 43, 77–90 (1979)) with EcoRV and BalI. Into the EcoRI-HindIII of the pBR322 fragment is incorporated the EcoRI-HindIII of pUC119 multicloning site (Vieria, J. and Messing, J., Methods in Enzymology, 153, 3–11 (1987)) to produce a plasmid ApBR Mcs in which the VspI-ScaI sequence of pBR322 is then replaced by the VspI-ScaI sequence of pUC119 with deletion of PstI present in the VspI-ScaI of pBR322 so as to afford the desired pBM vector (3122 bp). In the pBM, there are present restriction sites: PstI$^{36}$, HindIII$^{49}$, VspI$^{2298}$, ScaI$^{2605}$, and EcoRI$^{3120}$, together with an ampicillin resistance sequence (Amp) and a replication origin (Ori).

Ten μl of the ligation reaction mixture obtained was then transformed into Escherichia coli strain JM109. The compitent E. coli strain has previously been made by the rubidium chloride method (Hanahan, DNA cloning: A practical approach, IRC Press (1985)).

The transformed E. coli was then cultured at 37° C. overnight on LB-Amp plate (1% tryptone, 0.5% yeast extract, 0.5% NaCl, 1.5% agar, ampicillin (50 μg/ml)). One colony generated on the plate was picked up and cultured in LB medium (1% tryptone, 0.5% yeast extract, 0.5% NaCl) containing 50 μg/ml of ampicillin with shaking at 37° C. overnight. 1.5 ml of the culture was centrifuged to collect the bacterial cells which were subjected to mini-preparation in accordance with the alkaline method (Maniatis et al., supra) in order to obtain a plasmid DNA. One μg of the obtained plasmid DNA was digested at 37° C. for 1 hr in 30 μl of reaction solution (100 mM Tris-HCl pH 7.5, 50 mM NaCl, 7 mM MgCl$_2$, 10 units each of EcoRI and HindIII (ex Takara Shuzo), and the digest was subjected to size analysis by agarose gel electrophoresis to confirm an about 700 bp insert DNA fragment. The clone containing the insert DNA fragment was named C14-8. The C14-8 DNA fragment was sequenced for nucleotide sequence by the Sanger's dideoxy chain termination procedure, by which its deduced amino acid sequence was also determined. The determined amino acid and nucleotide sequence are shown in SEQ ID NO:9.

In order to prepare C14-2-2 DNA fragment from the C14-8 DNA, PCR was carried out in the same manner as above excepting use of the following primers:

5'-GCGAATTCGCGACCGGGTGTGTTTCCAT-3' (SEQ ID NO:27); and
5'-TCATTAGAACTGCTCCACCTTGGGCCA-3' (SEQ ID NO:28).

One ng of the C14-8 DNA as template was mixed with 50 pmoles each of the above primers, 67 mM Tris-HCl (pH8.8), 16.6 mM $(NH_4)_2SO_4$, 0.2 mM dNTPs, 2 mM $MgCl_2$, 0.2 mg/ml gelatine, and 0.05% Triton X-100 in a total volume of 50 µl, and 2.5 units of Taq DNA polymerase was further added to the mixture. Following overlay of paraffin oil, PCR was undergone (94° C. for 30 sec, 55° C. for 60 sec, 72° C. for 120 sec, 30 cycles). The reaction mixture was subjected to agarose gel electrophoresis to isolate an approximately 260 bp fragment which was subsequently recovered into 50 µl of TE buffer (10 mM Tris-HCl (pH 7.5), 1 mM EDTA) by the Glass powder method (Gene Clean II; ex BIO101). To the recovered DNA solution (25 µl) were added 3 µl of 10×T4 buffer (0.5M Tris-HCl (pH 7.5), 100 mM $MgCl_2$, 100 mM DTT), 3 µl of 2 mM dNTPs, and 3 µl of ATP, and then 5 units of DNA polymerase I (ex New England Biolab) and 10 units of T4 polynucleotidyl kinase (ex Takara Shuzo) were further added to the mixture in order to allow to react at 37° C. for 1 hr. The desired DNA fragment was recovered into 25 µl of TE solution by the Glass powder method.

On the other hand, 1 µg of pUC118 (Vieira, J., supra) was cleaved by restriction reaction in 20 µl of restriction solution (10 mM Tris-HCl (pH 8.0), 7 mM $MgCl_2$, 20 mM KCl, 10 units of SmaI) at 37° C. for 1 hr. To the reaction mixture were added 10 µl of 1M Tris-HCl (pH 8.0), 70 µl of sterilized water and 2 units of bacterial alkaline phosphatase (ex Takara Shuzo) in order to allow to react at 68° C. for 30 min. Following the reaction, DNA in the solution was extracted with a phenol/chloroform mixed solution and then precipitated with ethanol. After the recovered DNA (10 µl) was dissolved in 10 ml of the TE buffer, 1 µl of the solution was mixed with 10 µl of the above-described PCR DNA fragment to which 50 µl of Ligation liquid A and 10 µl of Ligation liquid B (DNA Ligation Kit; ex Takara Shuzo) were then added and mixed well in order to allow to react 16° C. for 1 hr. Ten µl of the obtained DNA solution was transformed into *E. coli* strain XL1-blue (ex Stratagene) in accordance with the Hanahan's method (Hanahan, supra).

Recombinant plasmid DNA was recovered from the resulting clone. 1.5 µg of the plasmid DNA was then allowed to react in the presence of M13RP1 primer (ex Applied Biosystems) or −21M13 primer (ex Applied Biosystems) in accordance with the Cycling sequencing procedure (see Technical manual made by Applied Biosystems). The reaction product was analyzed on DNA sequencer Model 370A (version 1. 30; ex Applied Biosystems) to determine its nucleotide sequence shown in SEQ ID NO:8. This DNA fragment (C14-2-2) codes for the peptide having amino acid sequence shown in SEQ ID NO:4.

Construction of Expression Vector

One µg of the pUC.C14-2-2 DNA was digested in 20 µl of restriction solution (50 mM Tris-HCl (pH 7.5), 100 mM NaCl, 7 mM $MgCl_2$, 10 units each of EcoRI and SalI (ex Takara Shuzo)) at 37° C. for 1 hr and sequentially subjected to agarose gel electrophoresis and to the Glass powder procedure so as to purify the desired DNA. On the other hand, one µg of the expression vector pAT.trp.trpE DNA (JP-A-1-215,289) was treated under the same conditions to obtain a vector DNA fragment. The resulting EcoRI-SalI treated vector DNA (1 µg) was ligated with the C14-2-2 DNA fragment prepared above at 16° C. for 1 hr, using DNA ligation kit (ex Takara Shuzo) in accordance with the procedure recommended by the mixer.

Ten µl of the reaction mixture obtained was transformed into *Escherichia coli* strain C600. The compitent *E. coli* strain for transformation has been made by the Hanahan's method (Hanahan, supra). The transformed cells was plated on LB-plate (1% tryptone, 0.5% yeast extract, 0.5% NaCl, 1.5% agar) containing 50 µg/ml of ampicillin, and stored at 37° C. overnight. One platinum loop of colonies generated on the plate was picked up and cultured in the LB medium containing 50 µg/ml ampicillin at 37° C. overnight. The obtained culture (1.5 ml) was centrifuged to collect bacterial cells and subjected to mini-preparation of plasmid DNA by the alkaline method (Maniatis ea al., supra).

The resulting DNA (1 µg) was doubly digested with EcoRI and SalI, and in the digests the expression plasmid pAT.trp.trpE C14-2-2 was screened from which an about 260 bp EcoRI-SalI fragment can be produced.

EXAMPLE 4

Expression and Purification of Peptides Encoded by C14-1, C14-1-2, C14-2, C14-2-1 and C14-2-2 DNA Fragments

*Eschericia coli* C600 cells carrying each of the five expression plasmids constructed in Examples 1 to 3 were inoculated into 40 ml of the LB-medium containing 50 µg/ml of ampicillin, and subcultured therein at 37° C. overnight. The culture (50 ml) was further inoculated into 4 liters of M9-CA medium (0.6% $Na_2HPO_4$, 0.5% $KH_2PO_4$, 0.5% NaCl, 0.1% $NH_4Cl$, 0.1 mM $CaCl_2$, 2 mM $MgSO_4$, 0.5% casaamino acids, 0.2% glucose) and cultured at 37° C. When $OD_{600}$ reached 0.3, indoleacrylic acid was added to the culture to a final concentration of 40 µg/l and the cultivation was continued for further 16 hr. The culture was centrifuged to collect about 12 g of bacterial cells. To the cells was added 60 ml of lysis buffer (50 mM Tris-HCl (pH 8.0), 30 mM NaCl, 5 mM EDTA), after which 12 mg of lysozyme (ex Seikagaku Kogyo KK) was added to the mixture to allow to react at 37° C. for 1 hr. After the *E. coli* cells were disrupted by sonication for 150 sec, the centrifugation carried out at 15,000 rpm at 4° C. for 15 min to separate an insoluble fraction containing a fused peptide which was composed of a peptide encoded by the desired DNA and trpE. 55 ml of solubilization buffer (4M urea, 50 mM Tris-HCl (pH 8.0), 0.1% NP-40) was added to the fraction in order to extract the fused peptide.

To the extract were added urea and DTT to final concentrations of 6M and 50 mM, respectively. After standing at 4° C. for at least 1 hr, the mixture was applied to Mono Q column (ex Pharmacia) equilibrated with 50 mM Tris-HCl (pH 8.5) containing 6M urea and 5 mM DTT. The desired peptide was then eluted from the column using NaCl gradient of 0M to 0.2M. The eluted fractions were pooled and applied to HiLoad Superdex 75 pg column (ex Pharmacia) equilibrated with 50 mM Tris-HCl (pH 8.5) containing 6M urea, 0.15M NaCl and 5 mM DTT in order to purify the fused peptide.

By the above-mentioned procedure, the following were obtained: trp.C14-1 (Mr, about 8 kDa); trpE.C14-1-2 (Mr, about 11 kDa); trpE.C14-2 (Mr, about 10 kDa); trpE.C14-2-1 (Mr, about 6 kDa); and trpE.C14-2-2 (Mr, about 11 kDa).

EXAMPLE 5

Preparation of C14-1, C14-1-2, C14-2 and C14-2-2 Peptide Fragments

Peptide fragments were synthesized using Applied Biosystems Peptide Synthesizer Model 430A (ex Applied Biosystems) in accordance with the attached protocol of Fast Moc system. At the end of synthesis, deprotection and deresin were carried out by conventional methods, followed by the purification of the peptide fragments by HPLC.

The desired peak was collected and analyzed for amino acid contents using an amino acid analyzer JLC-300 (ex JEOL LTD) or for amino acid sequence using a protein sequencer Model 477A (ex Applied Biosystems) in order to confirm to be a desired peptide.

EXAMPLE 6

Measurement of HCV Antibodies in Sera from Hepatitis C Patients (i) Detection of HCV Antibodies by Western Blot Analysis:

The expressed peptide trpE.C14-2 (1 μg) was subjected to SDS-polyacrylamide gel electrophoresis (Laemmli, Nature 227, 680 (1970)), and transferred to a nitrocellulose filter (ex Bio-Rad). The filter was dipped in blocking solution (4% Block-Ace (ex Snow Brand Milk Products Co.), 2% BSA, 0.1M sodium phosphate (pH 7.4)) at room temperature for 1 hr. Thereafter, the peptide on the filter was allowed to react with sera (diluted in 1/100) from healthy human and hepatitis C patients at room temperature for 1 hr. After the filter was washed with wash solution (20 mM Tris-HCl (pH 7.5), 500 mM NaCl, 0.05% Tween-20), the filter was allowed to react with peroxidase-labeled goat anti-human IgG (diluted in 1/1000) at room temperature for 30 min. Following washing again, the filter was dipped in a diaminobenzidine (as substrate) solution. Once the color development was confirmed, the reaction was stopped by dipping the filter in pure water.

Figure 3:
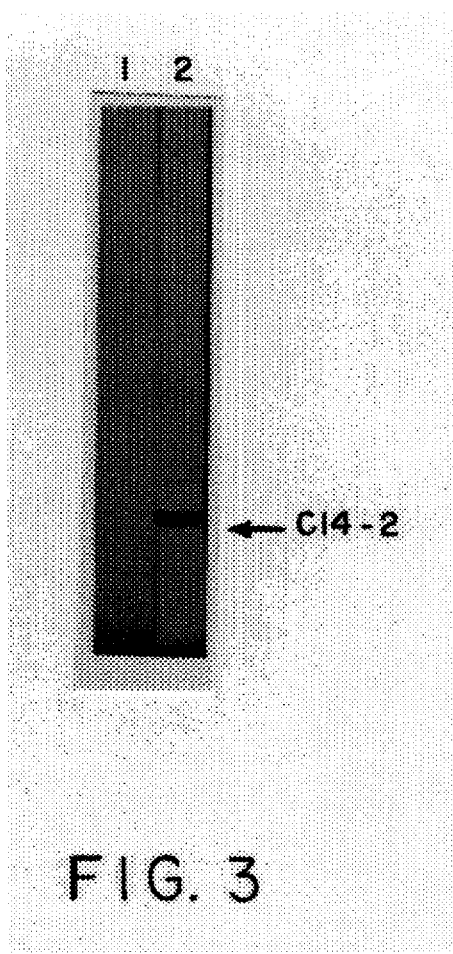
FIG. 3 shows an western blot photograph illustrating an antigen-antibody reaction of the expressed peptide trpE.C14-2 with a serum from a patient suffering from hepatitis C (see lane 2). Control is a serum from a healthy human (see lane 1).

As shown in FIG. 3, The expressed peptide was strongly reacted with the patient's sera but not with serum from healthy human, and thus the peptide could be detected as specific band on the western blotted filter.

(ii) Grouping of HCV by Enzyme-Immunoassay (ELISA) (A):

Various sera from Japanese chronic hepatitis C patients were tested for grouping of HCV by ELISA using the fused peptides trpE.C14-1, trpE.C14-1-2, trpE.C14-2, trpE.C14-2-1 and trpE.C14-2-2. The ELISA was carried out in the conventional manner as follows: A purified antigen was diluted with 0.1M phosphate buffer (pH 7.5) containing 8M urea to a final concentration of 5 μg/ml, and then immobilized on a microplate at 4° C. or room temperature. After washing with a wash solution several times, diluted sera to be tested were placed in wells of the plate and the incubation was carried out at 30° C. or room temperature for 1 hr. Following washing, to each well was added peroxidase-labeled anti-human IgG (mouse monoclonal antibody) in order to allow to react at 30° C. or room temperature. The plate was washed several times followed by addition of 50 μl of o-phenylenediamine solution so as to occur coloration at 37° C. The color development was subsequently stopped by addition of 2M $H_2SO_4$ and its absorbance at 492 nm was determined using a color comparator. At the same time, healthy human sera as control were measured in the same way, as well as commercially available Chiron kit C100-3 (ex Ortho) for comparison. The results are shown in Tables 1, 2, 3 and 4.

The Tables 1, 2, 3 and 4 indicate that both the fused peptides trpE.C14-1 and trpE.C14-1-2 can recognize antibodies to HCV Group I specifically while the fused peptides trpE.C14-2, trpE.C14-2-1 and trpE.C14-2-2 can recognize antibodies to HCV Group II specifically. In addition, the results show that the peptides used are very useful in determining whether hepatitis C patients have been infected with HCV Group I alone or HCV Group II alone or both HCV Groups I and II, when C14-1 and/or C14-1-2 peptides are used in combination with C14-2 and/or C14-2-1 and/or C14-2-2 peptides.

TABLE 1

| Sample No. | trpE.C14-2 (Group II) | Chiron Kit (C100-3) (Group I) |
|---|---|---|
| 1 | + | − |
| 2 | + | − |
| 3 | + | − |
| 4 | + | − |
| 5 | − | + |
| 6 | + | − |
| 7 | − | + |
| 8 | + | − |
| 9 | − | + |
| 10 | + | − |
| 11 | + | − |
| 12 | − | + |
| 13 | − | + |
| 14 | − | + |
| 15 | − | + |
| Negative Control | − | − |

TABLE 2

| Sample No. | trpE.C14-2-1 (Group II) | trpE.C14-2 (Group II) |
|---|---|---|
| 16 | + | + |
| 17 | − | − |
| 18 | + | + |
| 19 | − | − |
| 20 | − | − |
| 21 | + | + |
| 22 | − | − |
| 23 | − | − |
| 24 | − | − |
| 25 | − | − |
| 26 | + | + |
| 27 | − | − |
| Negative Control | − | − |

TABLE 3

| Sample No. | trpE.C14-1 (Group I) | trpE.C14-2 (Group II) |
|---|---|---|
| 28 | − | + |
| 29 | + | − |
| 30 | + | − |
| 31 | + | − |
| 32 | + | − |
| 33 | + | − |
| 34 | + | − |
| 35 | + | − |
| 36 | + | − |
| 37 | − | + |
| 38 | + | − |
| 39 | + | − |
| 40 | − | + |
| 41 | + | − |
| 42 | − | + |
| 43 | + | − |
| 44 | + | − |
| 45 | + | − |
| 46 | + | − |
| 47 | − | + |
| Negative Control | − | − |

TABLE 4

| Sample No. | trpE.C14-1 (Group I) | trpE.C14-1-2 (Group I) | trpE.C14-2 (Group II) | trpE.C14-2-2 (Group II) |
|---|---|---|---|---|
| 47 | − | − | + | + |
| 48 | + | + | − | − |
| 49 | + | + | − | − |
| 50 | + | + | − | − |
| 51 | + | + | − | − |
| 52 | + | + | − | − |
| 53 | + | + | − | − |
| 54 | + | + | − | − |
| 55 | + | + | − | − |
| 56 | − | − | + | + |
| 57 | + | + | − | − |
| 58 | + | + | − | − |
| 59 | − | − | + | + |
| 60 | + | + | − | − |
| 61 | − | − | + | + |
| 62 | + | + | − | − |
| 63 | + | + | − | − |
| 64 | + | + | − | − |
| 65 | + | + | − | − |
| Negative Control | − | − | − | − |

(iii) Grouping of HCV by ELISA (B):

Various sera from Japanese chronic hepatitis C patients were tested for grouping of HCV by ELISA using trpE.C14-1, trpE.C14-2-2, and the C14-1, C14-1-2, C14-2 and C14-2-2 peptide fragments prepared in Example 5 (1-Y, 1-Z, 1-B, 2-Y, 2-B and 2-Z).

The trpE.C14-1-2 or trpE.C14-2-2 was previously immobilized in wells of a microplate in the same way as above. Twenty μl of specimen was mixed with 20 μl of each peptide (0.1 mg/ml) synthesized in Example 5 and left to stand at room temperature for 1 hr. 200 μl of diluted specimen was added to the peptide solution which was then placed in wells of the plate. After reaction at 30° C. for 1 hr followed by washing, the plate was allowed to react with peroxidase-labeled anti-human IgG (mouse monoclonal antibody) at 30° C. for 1 hr. After washing, o-phenylenediamine solution was added to the reaction mixture to react at 30° C. for 1 hr. The reaction was stopped by addition of 1M sulfuric acid solution and the color development was determined for absorbance at 492 nm using a color comparator. For comparison, the commercially available HCV diagnosis reagent "Immucheck-HCV" (ex International Reagents Corporation) was used in immunological reaction.

The result are shown in Tables 5, 6 and 7.

The fact that all the specimens described in Table 5 belong to HCV Group I can be seen from the results of the reaction with trpE.C14-1-2, and Table 5 also indicates that the reaction of the specimens with trpE.C14-1-2 is inhibited by addition of the peptides having HCV Group I sequences prepared in Example 5. The fact that all the specimens described in Table 7 belong to HCV Group II can be seen from the results of the reaction with trpE.C14-2-2, and Table 7 also indicates that the reaction of the specimens with trpE.C14-2-2 is inhibited by addition of the peptides having HCV Group II sequences prepared in Example 5. Moreover, The fact that all the specimens described in Table 6 belong to both HCV Groups I and II can be seen from the results of the reaction with trpE.C14-1-2 or trpE.C14-2-2, and Table 6 also indicates that the reaction of the specimens with trpE.C14-1-2 or trpE.C14-2-2 is inhibited by addition of the peptides having HCV Group I or II sequences prepared in Example 5.

Therefore, it has been found that trpE.C14-1-2 or trpE.C14-2-2 can specifically react with anti-HCV antibodies, and that one can determine whether the patients have been infected with HCV Group I alone or HCV Group II or both HCV Groups I and II by measuring the inhibition of the immunological reaction of trpE.C14-1-2 or trpE.C14-2-2 with anti-HCV antibodies by the peptide fragments prepared in Example 5. Thus, the peptide fragments are also useful in grouping HCV. On the contrary, The grouping by the Immucheck-HCV was difficult as seen in Tables 5, 6 and 7.

TABLE 5

| | COI[1) | Absorbance at 492 nm | | |
|---|---|---|---|---|
| Sample No. | Immuchek HCV | trpE.C14-1-2 | Inhibiting peptide | trpE.C14-2-2 |
| CH 45 | 7.72< | 3.000< | (1-Y) | 0.168 |
| CH 94 | 7.72< | 3.000< | (1-Y = Z)[2) | 0.057 |
| LC 31 | 7.72< | 2.300 | (1-Z > B > Y)[3) | 0.043 |
| HCC 10 | 7.72< | 3.000< | (1-Y) | 0.023 |
| HCC 25 | 7.72< | 3.000< | (1-Z = B)[4) | 0.268 |
| LC 25 | 7.72< | 1.750 | (1-Z) | 0.049 |
| LC 92 | 7.72< | 0.554 | (1-Z) | 0.004 |

[1)COI: cut off index.
[2)1-Y = Z: 1-Y and 1-Z inhibit the reaction of anti-HCB antibodies with trpE.C14-1-2 to the same extent.
[3)1-Z > B > Y: 1-Z, 1-B and 1-Y inhibit said reaction in the order of 1-Z > 1-B > 1-Y.
[4)1-Z = B: 1-Z and 1-B inhibit said reaction to the same extent.

TABLE 6

| | COI[1) | Absorbance at 492 nm | | | |
|---|---|---|---|---|---|
| Sample No. | Immuchek HCV | trpE. C14-1-2 | Inhibiting peptide | trpE. C14-2-2 | Inhibiting Peptide |
| CH 11 | 7.72< | 3.000< | (1-Z) | 3.000< | (2-B > Y)[3) |
| CH 36 | 7.72< | 3.000< | (1-Y) | 3.000< | (2-Y) |
| LC 66 | 7.72< | 2.995 | (1-Z) | 2.559 | (2-Y) |
| HCC 88 | 7.72< | 1.088 | (1-Z) | 0.833 | (2-Y > Z > X)[4) |
| LC 13 | 7.72< | 2.800 | (1-Z = Y)[2) | 2.081 | (2-Y) |
| CH 82 | 7.72< | 2.961 | (1-Y) | 0.761 | (2-Y = B) |
| HCC 71 | 7.72< | 2.559 | (1-Z) | 0.748 | (2-B) |
| HCC 93 | 7.72< | 3.000< | (1-Y) | 0.495 | (2-B) |
| LC 71 | 7.72< | 1.967 | (1-Y) | 2.363 | (2-Y = B) |

[1)COI: cut off index.
[2)1-Z = Y: 1-Z and 1-Y inhibit the reaction of anti-HCV antibodies with trpE.C14-1-2 to the same extent.
[3)2-B > Y: 2-B and 2-Y inhibiti the reaction of anti-HCV antibodies with trpE.C14-2-2 in the order of 2-B > 2-Y.
[4)2-Y > Z > X: 2-Y, 2-Z and 2-X inhibit said reaction in the order of 2-Y > 2-Z > 2-X.
[5)2-Y = B: 2-Y and 2-B inhibit said reaction to the same extent.

TABLE 7

| | COI[1) | Absorbance at 492 nm | | |
|---|---|---|---|---|
| Sample No. | Immuchek HCV | trpE.C14-1-2 | trpE.C14-2-2 | Inhibiting peptide |
| CH 20 | 7.72< | 0.128 | 3.000< | (2-Z = B)[2) |
| LC 69 | 7.72< | 0.098 | 3.000< | (2-B) |
| HCC 51 | 7.72< | 0.027 | 2.978 | (2-Y) |

[1)COI: cut off index.
[2)2-Z = B: 2-Z and 2-B inhibit the reaction of anti-HCV antibodies with trpE.C14-2-2 to the same extent.

(iv) Grouping of HCV by ELISA (C):

The peptide fragments (1-Z, 1-Y) prepared in Example 5 were immobilized in wells of a microplate. To each well were added sera from hepatitis C patients. After reaction in the same manner as in (ii), absorbance was determined at 492 nm. The results are shown in Table 8. As seen in the table, the grouping of HCV can be carried out using peptide fragments such as 1-Z and 1-Y. However, some specimens reacted with only "Z" or "Y", suggesting that the peptide fragment is preferably one that at least two peptides have been combined or bound to one another.

TABLE 8

| Serum No. | Inhibiting peptide | Reacting peptide | C14-1-2 |
|---|---|---|---|
| 20 | 1-Z | 1-Y | + |
| 25 | 1-Y | 1-Y | + |
| 26 | 1-Z | 1-Y, 1-Z | + |
| 28 | 1-Z | 1-Z | + |
| 30 | 1-Y | 1-Y | + |

EXAMPLE 7

Preparation of Kit

The purified antigens (as Groups I and II) are individually diluted with phosphate buffer containing 8M urea to a final concentration of 5 μg/ml. The individual diluted solutions are placed in different multiplates in an amount of 100 μl per well, and left to stand at 4° C. overnight. The solutions are decanted from the plates and a blocking solution (300 μl/well) is placed in wells of the plates followed by standing at room temperature for 2 hr. After decantation, the wells are washed and then freeze-dried. Each of the freeze-dried plates (as Groups I and II) is placed in a different bag or pouch, sealed, packaged in a box for kit, and stored at 4° C. In the kit, the following reagents in different containers (e.g., bottle or vial) are also placed: preconfirmed positive sera capable of reacting specifically with HCV Groups I and II, respectively; dilution liquid for diluting sera as test samples; wash liquid; enzyme-labeled anti-human IgG mouse monoclonal antibody; and color development liquid.

EXAMPLE 8

Correlation of Interferon (IFN)-Treatment Effect with Grouping of HCV by RT-PCR

Correlation of IFN-treatment effect with the grouping of HCV by RT-PCR was examined using a set of the primers which can specifically detect HCV Groups I and II respectively, as follows:

100 μl of hepatitis C patient's serum was mixed with 300 μl of 6M GTC solution (6M guanidine thiocyanate, 25 mM sodium citrate, 0.5% sarkosyl, 0.2M β-mercaptoethanol). To the mixture were further added 40 μl of 2M sodium acetate (pH 5.2), 400 μl of phenol and 80 μl of chloroform/isoamyl alcohol (49:1) with stirring. The aqueous layer was removed to which isoprpopyl alcohol was then added and centrifuged to afford a RNA precipitation for cDNA synthesis. The cDNA synthesis was carried out in the reaction mixture (10 mM Tris-HCl, 0.01% gelatine, 1 mM DTT, 100 pmol of primers) containing the RNA precipitation, in the presence of RNase inhibitor and reverse transcriptase at 37° C. for 2 hr. The cDNA obtained was used in the two-step PCR.

PCR was undergone as follows: To 100 μl of the reaction mixture (containing cDNA) prepared above were added 10 mM Tris-HCl, 0.01% gelatine, 2 mM each dNTPs, 1.5 mM MgCl$_2$ and the primers (50 pmol each; see below). PCR conditions used were: denaturation, 94° C. for 1.5 min; annealing, 50° C. for 2 min; extension, 70° C. for 2 min; 35 cycles. Of primers examined, the following four primers enabled the detection of a 206 bp DNA fragment specific for HCV Group II:

primers used in a first step PCR:

KK21: 5'-GGATACACCGGTGACTTTGA-3' (SEQ ID NO:29); and
KK22: 5'-TGCATGCACGTGGCGATGTA-3' (SEQ ID NO:30);

primers used in a second step PCR:

KK26: 5'-GATGCCCACTTCCTCTCCCA-3' (SEQ ID NO:31); and
KK27: 5'-GTCAGGGTAACCTCGTTGGT-3' (SEQ ID NO:32).

On the other hand, a 153 bp DNA fragment specific for HCV Group I could be detected by use of the following four primers:

primers used in a first step PCR:

KK1: 5'-GGCTATACCGGCGACTTCGA-3' (SEQ ID NO:33); and
KK2: 5'-GACATGCATGTCATGATGTA-3' (SEQ ID NO:34);

primers used in a second step PCR:

KK5: 5'-GATCGACTGTAACACATGTG-3' (SEQ ID NO:35); and
KK8: 5'-CACATTTGATCCCACGATGG-3' (SEQ ID NO:36).

The results are shown in Table 9. The table indicates that 78% of nine sera from the patients having a marvelous efficacy of IFN belong to Group II while 22% thereof to Group I, and therefore that major patients having IFN-treatment effect have been infected with HCV Group II.

As seen in the examples described above, the antigenic peptides or the kit comprising the same of the present invention can be used to determine whether a hepatitis C patient has been infected with HCV Group I or HCV Group II or both HCV Groups I and II (i.e., mixed infection). If the patient is found to be infected with HCV Group II, the patient will be able to receive early IFN treatment effectively on the basis of the fact that the IFN treatment is particularly effective against HCV Group II. The peptides and kit of the present invention are also useful for diagnosis of HCV infection.

TABLE 9

| Hepatitis C patient No. | IFN-treatment effect | Result of grouping |
|---|---|---|
| 1 | ME[1] | I |
| 2 | ME | II |
| 3 | ME | I |
| 4 | ME | II |
| 5 | ME | II |
| 6 | ME | II |
| 7 | transient | I |
| 8 | transient | I |
| 9 | transient | II |
| 10 | transient | I |
| 11 | transient | I |
| 12 | no effect | I |
| 13 | no effect | I |
| 14 | no effect | I |
| 15 | no effect | I |
| 16 | no effect | I |
| 17 | transient | I |

TABLE 9-continued

| Hepatitis C patient No. | IFN-treatment effect | Result of grouping |
|---|---|---|
| 18 | no effect | I |
| 19 | no effect | I |
| 20 | ME | II |
| 21 | no effect | I |
| 22 | transient | I |
| 23 | ME | II |
| 24 | ME | II |
| 25 | transient | I |

[1]ME: marvelous effect

What is claimed is:

1. An antigenic peptide having an amino acid sequence shown in SEQ ID NO:3 or SEQ ID NO:4 and capable of reacting specifically with antibodies directed against Group II of hepatitis C virus.

2. A method for grouping hepatitis C virus, which comprises:

contacting the antigenic peptide according to claim 1 with a specimen presumed to contain antibodies to hepatitis C virus in order to carry out an immunological reaction; and detecting antibodies directed against hepatitis C virus belonging to Group II as positive.

3. A kit for identifying Group I or Group II of hepatitis C virus, which comprises in separate sections at least one first antigenic peptide selected from the group consisting of peptides having amino acid sequences shown in SEQ ID NO:1 and SEQ ID NO:2 and capable of reacting specifically with antibodies directed against Group I of hepatitis C virus; and at least one second antigenic peptide selected from the group consisting of peptides having amino acid sequences shown in SEQ ID NO:3 and SEQ ID NO:4 and capable of reacting specifically with antibodies directed against Group II of hepatitis C virus.

4. A method for grouping hepatitis C virus, which comprises:

contacting at least one first peptide selected from the group consisting of peptides having amino acid sequences shown in SEQ ID NO:1 and SEQ ID NO:2 and being capable of reacting specifically with antibodies directed against Group I of hepatitis C virus, and at least one second peptide selected from the group consisting of peptides having amino acid sequences shown in SEQ ID NO:3 and SEQ ID NO:4 and being capable of reacting specifically with antibodies directed against Group II of hepatitis C virus, individually with a specimen presumed to contain antibodies to hepatitis C virus so as to determine the antibodies quantitatively or qualitatively by immunological reaction, the first and second peptides being included in the kit as defined in claim 7, and detecting the antibodies to Group I or Group II of hepatitis C virus.

5. A kit for identifying Group I or Group II of hepatitis C virus, which comprises in separate sections: a first antigenic peptide having an amino acid sequence shown in SEQ ID NO:2 and capable of reacting specifically with antibodies directed against Group I of hepatitis C virus; and a second antigenic peptide having an amino acid sequence shown in SEQ ID NO:4 and capable of reacting specifically with antibodies directed against Group II of hepatitis C virus.

6. A method for grouping hepatitis C virus, which comprises:

contacting a first antigenic peptide having an amino acid sequence shown in SEQ ID NO:2 and capable of reacting specifically with antibodies directed against Group I of hepatitis C virus and a second antigenic peptide having an amino acid sequence shown in SEQ ID NO:4 and capable of reacting specifically with antibodies directed against Group II of hepatitis C virus, the first and second peptides being contained in the kit according to claim 5, individually with a specimen presumed to contain antibodies to hepatitis C virus so as to determine the antibodies quantitatively or qualitatively by immunological reaction; and detecting the antibodies to Group I or Group II of hepatitis C virus.

7. A kit for identifying Group I or Group II of hepatitis C virus, which comprises in separate sections at least one first antigenic polypeptide selected from the group consisting of fusion polypeptides with trpE, containing amino acid sequences shown in SEQ ID NO:1 and SEQ ID NO:2 and capable of reacting specifically with antibodies directed against Group I of hepatitis C virus; and at least one second antigenic polypeptide selected from the group consisting of fusion polypeptides with trpE, containing amino acid sequences shown in SEQ ID NO:3 and SEQ ID NO:4 and capable of reacting specifically with antibodies directed against Group II of hepatitis C virus.

8. A method for grouping hepatitis C virus, which comprises:

contacting at least one first antigenic polypeptide selected from the group consisting of fusion polypeptides with trpE, containing amino acid sequences shown in SEQ ID NO:1 and SEQ ID NO:2 and capable of reacting specifically with antibodies directed against Group I of hepatitis C virus, and at least one second antigenic polypeptide selected from the group consisting of fusion polypeptides with trpE, containing amino acid sequences shown in SEQ ID NO:3 and SEQ ID NO:4 and capable of reacting specifically with antibodies directed against Group II of hepatitis C virus, individually with a specimen presumed to contain antibodies to hepatitis C virus so as to determine the antibodies quantitatively or qualitatively by immunological reaction; and detecting the antibodies to Group I or Group II of hepatitis C virus.

* * * * *